(12) United States Patent
Madsen et al.

(10) Patent No.: US 7,462,488 B2
(45) Date of Patent: Dec. 9, 2008

(54) TISSUE MIMICKING ELASTOGRAPHY PHANTOMS

(75) Inventors: Ernest L. Madsen, Madison, WI (US); Gary R. Frank, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 455 days.

(21) Appl. No.: 11/140,400

(22) Filed: May 27, 2005

(65) Prior Publication Data

US 2005/0227364 A1    Oct. 13, 2005

Related U.S. Application Data

(62) Division of application No. 10/265,293, filed on Oct. 4, 2002, now abandoned.

(51) Int. Cl.
G01N 29/30 (2006.01)
G01N 31/00 (2006.01)

(52) U.S. Cl. .................. 436/8; 73/1.82; 73/1.86; 73/865.6; 73/866.4; 422/102; 600/442

(58) Field of Classification Search ............ 436/8, 436/173; 422/102; 73/1.82, 1.86, 865.6, 73/866.4; 252/408.1; 600/437, 442
See application file for complete search history.

(56) References Cited

U.S. PATENT DOCUMENTS

| | | | |
|---|---|---|---|
| 4,116,040 A | 9/1978 | Skoknecht et al. | |
| 4,277,367 A | 7/1981 | Madsen et al. | |
| 4,286,455 A | 9/1981 | Ophir et al. | |
| 4,331,021 A | 5/1982 | Lopez et al. | |
| 4,406,153 A | 9/1983 | Ophir et al. | |
| 4,417,582 A | 11/1983 | Trimmer et al. | |
| 4,453,408 A | 6/1984 | Clayman | |
| 4,470,303 A | 9/1984 | O'Donnell | |
| 4,542,745 A | 9/1985 | Oakley et al. | |
| 4,644,276 A | 2/1987 | Sierocuk et al. | |
| 4,729,892 A | 3/1988 | Beall | |
| 4,843,866 A | 7/1989 | Madsen et al. | |
| 5,054,310 A | 10/1991 | Flynn | |
| 5,164,978 A | 11/1992 | Goodenough et al. | |
| 5,196,343 A | 3/1993 | Zerhouni et al. | |
| 5,289,831 A | 3/1994 | Bosley | |
| 5,312,755 A | 5/1994 | Madsen et al. | |
| 5,336,999 A | 8/1994 | Mansfield et al. | |
| 5,474,070 A * | 12/1995 | Ophir et al. .............. 600/437 |
| 5,542,935 A | 8/1996 | Unger et al. | |

(Continued)

OTHER PUBLICATIONS

Letter from The University of Texas Professor Jonathan Ophir of Radiology to Assistant Vice President Dr. Bruce Butler dated Jan. 3, 2005.

(Continued)

Primary Examiner—Maureen M Wallenhorst
(74) Attorney, Agent, or Firm—Foley & Lardner LLP

(57) ABSTRACT

Tissue mimicking materials for elastography phantoms have elastic, ultrasound, and magnetic resonance characteristics that are characteristic of human soft tissues and well suited for the calibration and performance assessment of elastography imaging systems. In one embodiment, the material is formed from a base material containing an oil dispersed within a gel matrix and at least one inclusion formed from a gel. In another embodiment, the material is formed from a gel-forming material suffused throughout an open-cell reticulated mesh matrix.

27 Claims, 6 Drawing Sheets

U.S. PATENT DOCUMENTS

| | | | |
|---|---|---|---|
| 5,574,212 | A | 11/1996 | Madsen et al. |
| 5,625,137 | A | 4/1997 | Madsen et al. |
| 5,670,719 | A | 9/1997 | Madsen et al. |
| 5,756,875 | A | 5/1998 | Parker et al. |
| 5,779,392 | A | 7/1998 | Mendes |
| 5,827,942 | A | 10/1998 | Madsen et al. |
| 5,886,245 | A | 3/1999 | Flax |
| 5,902,748 | A | 5/1999 | Madsen et al. |
| 5,922,304 | A | 7/1999 | Unger |
| 5,951,475 | A | 9/1999 | Gueziec et al. |
| 6,008,644 | A | 12/1999 | Leunbach et al. |
| 6,011,626 | A | 1/2000 | Hielscher et al. |
| 6,148,655 | A | 11/2000 | Hall et al. |
| 6,190,915 | B1 | 2/2001 | Madsen et al. |
| 6,205,871 | B1 | 3/2001 | Saloner et al. |
| 6,238,343 | B1 | 5/2001 | Madsen et al. |
| 6,318,146 | B1 | 11/2001 | Madsen et al. |
| 6,352,860 | B1 | 3/2002 | Madsen et al. |
| 2002/0012999 | A1 | 1/2002 | Madsen et al. |

OTHER PUBLICATIONS

Letter from The University of Texas Professors Jonathan Ophir and Thomas A. Krouskop to Ms. Marnie Matt of the Wisconsin Alumni Research Foundation (WARF) dated Sep. 30, 2005 regarding Tissue Mimicking Elastography Phantoms, Madsen et al., US 2004/0067591 A1.

Letter from The University of Wisconsin Medical School Professor Emeritus Ernest L. Madsen, Ph. D. to Ms. Marnie A. Matt of the Wisconsin Alumni Research Foundation (WARF) dated Apr. 4, 2005 with accompanying items A-M.

Carson, Paul L., "What a Hospital Physicist Needs in a Transducer Characterization Standard: Are Tissue Equivalent Test Objects Necessary?" IEEE Transactions on Sonics and Ultrasonics, vol. S U-26, No. 1, Jan. 1979, pp. 1-6.

Smith, S.W. and H. Lopez, "A Contrast-Detail Analysis of Diagnostic Ultrasound Imaging," Med. Phys., vol. 9, No. 1, pp. 4-12, Jan./Feb. 1982.

Goldstein, et al., "Particle Image-Resolution Test Object," J. Ultrasound Med., vol. 2, May 1983, pp. 195-209.

Smith, et al., "Frequency Independent Ultrasound Contrast-Detail Analysis," Ultrasound in Med. & Biol., vol. 11, No. 3, pp. 467-477, May/Jun. 1985.

New Product Announcement, The Wisconsin Spherical Void Phantom, Oct. 1988.

Translation of German patent application No. 2814336, Feb. 1987.

D'Souza, Warren D. et al., "Tissue Mimicking Materials for a Multi-imaging Modality Prostate Phantom," Med. Phys. vol. 28, No. 4, pp. 688-700, Apr. 2001; published by Am. Assoc. Phys. Med.

Madsen, Ernest L. et al., "Ultrasonically Tissue-mimicking Liver Including the Frequency Dependence of Backscatter," Med. Phys. vol. 9, No. 5, pp. 703-710, Sep./Oct. 1982; published by Am. Assoc. Phys. Med.

Madsen, Ernest L. et al., "Liquid or Solid Ultrasonically Tissue-mimicking Materials with Very Low Scatter," Ultrasound in Med & Biol., vol. 24, No. 4, pp. 535-542, 1998; published by Elsevier Science Ltd.

de Korte, C. L. et al, "Elastic and Acoustic Properties of Vessel Mimicking Material for Elasticity Imaging," Ultrasonic Imaging, vol. 19, pp. 112-126; 1997; published by Dynamedia, Inc.

Steele, Derek D. et al., "Three-dimensional Static Displacement, Stimulated Echo NMR Elasticity Imaging," Phys. Med. Biol., vol. 45, pp. 1633-1648, 2000; published by IOP Publishing Ltd.

Ponnekanti, Hari et al., "Fundamental Mechanical Limitations on the Visualization of Elasticity Contrast in Elastography," Ultrasound in Med. & Biol., vol. 21, No. 4, pp. 533-543, 1995; published by Elsevier Science.

Parker, Kevin J. et al., "Vibration Sonoelastography and the Detectability of Lesions," Ultrasound in Med. & Biol., vol. 24, No. 9, pp. 1437-1447, 1998; published by Elsevier Science Ltd.

Bilgen, Mehmet et al., "Elastostatics of a Spherical Inclusion in Homogeneous Biological Media," Phys. Med. Biol., vol. 43, pp. 1-20, 1998; published by IOP Publishing Ltd.

Sinkus, R. et al, "High-resolution Tenor MR Elastography for Breast Tumour Detection," Phys. Med. Biol., vol. 45, pp. 1649-1664, 2000; published by IOP Publishing Ltd.

Weaver, John B. et al., "Magnetic Resonance Elastography Using 3D Gradient Echo Measurements of Steady-state Motion," Med. Phys., vol. 28, No. 8, pp. 1620-1628, Aug. 2001; published by Am. Assoc. Phys. Med.

Krouskop, Thomas A. et al., "Elastic Moduli of Breast and Prostate Tissues Under Compression," Ultrasonic Imagining, vol. 20, pp. 260-274, 1998; published by Dynamedia, Inc.

Hall, Timothy J. et al., "Phantom Materials for Elastography," IEEE Transactions on Ultrasonics, Ferroelectrics, and Frequency Control, vol. 44, No. 6, pp. 1355-1365, Nov. 1997; published by IEEE.

Ophir, Jonathan et al., "Optical and Acoustical Imaging of Biological Media," C. R. Acad. Sci. Paris, t. 2, Série IV, pp. 1193-1212, 2001; published by Académie des sciences.

Erkamp, R. Q. et al., "Exploiting Strain-hardening of Tissue to Increase Contrast in Elasticity Imaging," Biomedical Engineering, University of Michigan, Ann Arbor, Michigan, 2000; published IEEE Ultrasonics Symposium.

Van Houten, E. E. W. et al., "Elasticity Reconstruction from Experimental MR Displacement Data: Initial Experience with an Overlapping Subzone Finite Element Inversion Process," Med. Phys., vol. 27, No. 1, pp. 101-107, Jan. 2000; published by Am. Assoc. Phys. Med.

Kallel, Faouzi et al., "Contrast-Transfer Efficiency for Continuously Varying Tissue Moduli: Simulation and Phantom Validation," Ultrasound in Med. & Biol., vol. 27, No. 8, pp. 1115-1125, 2001; published by Elsevier Science Ltd.

Yeung, Fai et al., "Multilevel and Motion Model-Based Ultrasonic Speckle Tracking Algorithms," Ultrasound in Med. & Biol., vol. 24, No. 3, pp. 427-441, 1998; published by Elsevier Science Ltd.

Bishop, Jonathan et al., "Magnetic Resonance Imaging of Shear Wave Propagation in Excised Tissue," Sixth Meeting of the International Society of Magnetic Resonance in Medicine, Vancouver, British Columbia, pp. 1257-1265, 1997.

Gao, L. et al., "Sonoelasticity Imaging: Theory and Experimental Verification," J. Acoust. Soc. Am., vol. 97, No. 6, pp. 3875-3886, Jun. 1995; published by Acoustical Society of America.

Plewes, D. et al, "Visualization and Quantification of Breast Cancer Biomechanical Properties with Magnetic Resonance Elastography," Phys. Med. Biol., vol. 45, pp. 1591-1610, 2000; published by IOP Publishing Ltd.

Van Houten, E. E. W. et al., "An Overlapping Subzone Technique for MR-Based Elastic Property Reconstruction," Magnetic Resonance in Medicine, vol. 42, pp. 779-786, 1999; published by Wiley-Liss, Inc.

Kostelec, Peter J. et al., "Multiresolution Elastic Image Registration," Med. Phys., vol. 25, No. 9, p. 1593-1604, Sep. 1998; published by Am. Assoc. Phys. Med.

Van Houten, E. E. W. et al., "Three-Dimensional Subzone-Based Reconstruction Algorithm for MR Elastography," Magnetic Resonance in Medicine, vol. 45, pp. 827-837, 2001; published by Wiley-Liss, Inc.

O'Donnell, Matthew et al., "Internal Displacement and Strain Imaging Using Ultrasonic Speckle Tracking," IEEE Transactions on Ultrasonics, Ferroelectrics, and Frequency Control, vol. 41, No. 3, pp. 314-325, May 1994; published by IEEE.

Skovoroda, Andrei R. et al., "Reconstructive Elasticity Imaging for Large Deformations," IEEE Transactions of Ultrasonics, Ferroelectrics, and Frequency Control, vol. 46, No. 3, pp. 523-535, May 1999; published by IEEE.

Lubinski, Mark A. et al., "Speckle Tracking Methods for Ultrasonic Elasticity Imaging Using Short-Time Correlation," IEEE Transactions on Ultrasonics, Ferroelectrics, and Frequency Control, vol. 46, No. 1, pp. 82-96, Jan. 1999; published by IEEE.

Skovoroda, A. R. et al., "Tissue Elasticity Reconstruction Based on Ultrasonic Displacement and Strain Images," IEEE Transactions on Ultrasonics, Ferroelectrics, and Frequency Control, vol. 42, No. 4, pp. 747-765, Jul. 1995; published by IEEE.

Manduca, A. et al., "Image Processing for Magnetic Resonance Elastography," SPIE, vol. 2710, pp. 616-623, 1996.

Chaturvedi, Pawan et al., "Testing the Limitations of 2-D Companding for Strain Imaging Using Phantoms," *IEEE Transactions on Ultrasonics, Ferroelectrics, and Frequency Control*, vol. 46, No. 4, pp. 1022-1031, Jul. 1998; published by IEEE.

Zhu, Yanning et al., "Strain Imaging with a Deformable Mesh," *Ultrasonic Imaging*, vol. 21, pp. 127-146, 1999; published by Dynamedia, Inc.

Dutt, Vinayak et al., "Acoustic Shear-Wave Imaging Using Echo Ultrasound Compared to Magnetic Resonance Elastography," *Ultrasound in Med. & Biol.*, vol. 26, No. 3, pp. 397-403, 2000; published by World Federation for Ultrasound in Medicine & Biology.

Yamakawa, Makoto et al., "Tissue Elasticity Reconstruction Based on 3-Dimensional Finite-Element Model," *Jpn. J. Appl. Phys.*, vol. 38, pp. 3393-3398, 1999; published by Japanese Journal of Applied Physics.

Varghese, Tomy et al., "Multiresolution Imaging in Elastography," *IEEE Transactions on Ultrasonics, Ferroelectrics, and Frequency Control*, vol. 45, No. 1, pp. 65-75, 1998, published by IEEE.

Fu, D. et al., "Non-invasive Quantitative Reconstruction of Tissue Elasticity Using an Iterative Forward Approach," *Phys. Med. Biol.*, vol. 45, pp. 1495-1509, 2000; published by IOP Publishing Ltd.

Yeung, Fai et al., "Feature-Adaptive Motion Tracking of Ultrasound Image Sequences Using A Deformable Mesh," *IEEE Transactions on Medical Imaging*, vol. 17, No. 6, pp. 945-956, Dec. 1998; published by IEEE.

Erkamp, R. Q. et al., "Measuring the Elastic Modulus of Small Tissue Samples," *Ultrasonic Imaging*, vol. 20, pp. 17-28, 1998; published by Dynamedia, Inc.

Braun, Jürgen et al., "Simulation and Analysis of Magnetic Resonance Elastography Wave Images Using Coupled Harmonic Oscillators and Gaussian Local Frequency Estimation," *Magnetic Resonance Imaging*, vol. 19, pp. 703-713, 2001; published by Elsevier Science Inc.

Plewes, D. B. et al., "Visualizing Tissue Compliance with MR Imaging," *J. Magnetic Resonance Imaging*, vol. 5, pp. 733-738, 1995.

Muthupillai, R. et al., "Magnetic Resonance Elastography by Direct Visualization of Propagating Acoustic Strain Waves," *Science*, New Series, vol. 269, No. 5232, pp. 1854-1857, Sep. 29, 1995; published by The American Association for the Advancement of Science.

Romano, Anthony J. et al., "Evaluation of a Material Parameter Extraction Algorithm Using MRI-Based Displacement Measurements," *IEEE Transactions on Ultrasonics, Ferroelectrics, and Frequency Control*, vol. 47, No. 6, pp. 1575-1581, Nov. 2000; published by IEEE.

Muthupillai, Raja et al., "Magnetic Resonance Imaging of Transverse Acoustic Strain Waves," *MRM*, vol. 36, pp. 266-274, 1996; published by Williams & Wilkins.

Taylor, L. S. et al., "Three-dimensional Sonoelastography: Principles and Practices," *Phys. Med. Biol.*, vol. 45, pp. 1477-1494, 2000; published by IOP Publishing Ltd.

Walker, William F. et al., "A Method of Imaging Viscoelastic Parameters with Acoustic Radiation Force," *Phys. Med. Biol.*, vol. 45, pp. 1437-1447, 2000; published by IOP Publishing Ltd.

Chu, Kenneth C. et al., "Polyvinyl Alcohol Cryogel: An Ideal Phantom Material for MR Studies of Arterial Flow and Elasticity," *MRM*, vol. 37, pp. 314-319, 1997; published by Williams & Wilkins.

Fowlkes, J. B. et al., "Magnetic-Resonance Imaging Techniques for Detection of Elasticity Variation," *Med. Phys.*, vol. 22, No. 11, pp. 1771-1778, Nov. 1995; published by Am. Assoc. Phys. Med.

Wu, Tao et al., "MR Imaging Shear Waves Generated by Focused Ultrasound," *Magnetic Resonance in Medicine*, vol. 43, pp. 111-115, 2000; published by Wiley-Liss, Inc.

Bishop, Jonathan et al., "Two-Dimensional MR Elastography with Linear Inversion Reconstruction: Methodology and Noise Analysis," *Phys. Med. Biol.*, vol. 45, pp. 2081-2091, 2000; published by IOP Publishing Ltd.

Samani, Abbas et al., "A Constrained Modulus Reconstruction Technique for Breast Cancer Assessment," *IEEE Transactions on Medical Imaging*, vol. 20, No. 9, pp. 877-885, Sep. 2001; published by IEEE.

Bishop, Jonathan et al., "A Signal/Noise Analysis of Quasi-State MR Elastography," *IEEE Transactions on Medical Imaging*, vol. 20, No. 11, pp. 1183-1187, Nov. 2001; published by IEEE.

Blechinger, J. C. et al., "Tissue-Mimicking Gelatin-Agar Gels for Use in Magnetic Resonance Imaging," *Med. Phys.*, vol. 15, No. 4, pp. 629-636, Jul./Aug. 1988; published by Am. Assoc. Phys. Med.

Madsen, Ernest L. et al., "Low-Contrast Focal Lesion Detectability Phantom for $^1$H MR Imaging," *Med. Phys.*, vol. 18, No.3, pp. 549-554, May/Jun. 1991; published by Am. Assoc. Phys. Med.

Rice, J. Robin et al., "Anthropomorphic $^1$H MRS Head Phantom," *Med. Phys.*, vol. 25, No. 7, pp. 1145-1156, Jul. 1998, published by Am. Assoc. Phys. Med.

Madsen, Ernest L. et al., "Anthropomorphic Breast Phantoms for Assessing Ultrasonic Imaging System Performance and for Training Ultrasonographers: Part II," *J. Clin. Ultrasound*, vol. 10, pp. 91-100, Mar. 1982; published by John Wiley & Sons, Inc.

Madsen, Ernest L. et al., "Oil-In-Gelatin Dispersions for Use as Ultrasonically Tissue-Mimicking Materials," *Ultrasound in Med. & Biol.*, vol. 8, No. 3, pp. 277-287, 1982; published by Pergamon Press Ltd.

Samani, Abbas, "Biomechanical 3-D Finite Element Modeling of the Human Breast Using MRI Data," *IEEE Transactions on Medical Imaging*, vol. 20, No. 4, pp. 271-279, Apr. 2001; published by IEEE.

Madsen, Ernest L. et al., "Phantoms of Elastography," abstract submitted for the American Institute of Ultrasound in Medicine 46th Annual Convention, Mar. 2002.

Madsen, Ernest L. et al., "Stable Heterogeneous Phantoms for Testing Performance of US and MR Elastography Systems," abstract submitted for the First International Conference and Imaging of Tissue, Oct. 2002.

Insana, M. F., et al., "Ultrasonic Properties of Random Media Under Uniaxial Loading," *J. Acoust. Soc. Am.*, vol. 100, No. 6, pp. 3243-3251, Dec. 2001; published by the Acoustical Society of America.

* cited by examiner

FIG. 1 US elastogram (top left), MR elastogram (top right) and lateral (bottom left) and axial (bottom right) strain profiles for the phantom of Example 1.

FIG. 2  B-scan images (top left column), US elastograms (top right column) and lateral (bottom left) and axial (bottom right) strain profiles for the phantom of Example 2.

FIG. 3  US elastograms (top left and right) and lateral (bottom left) and axial (bottom right) strain profiles for the phantom of Example 3.

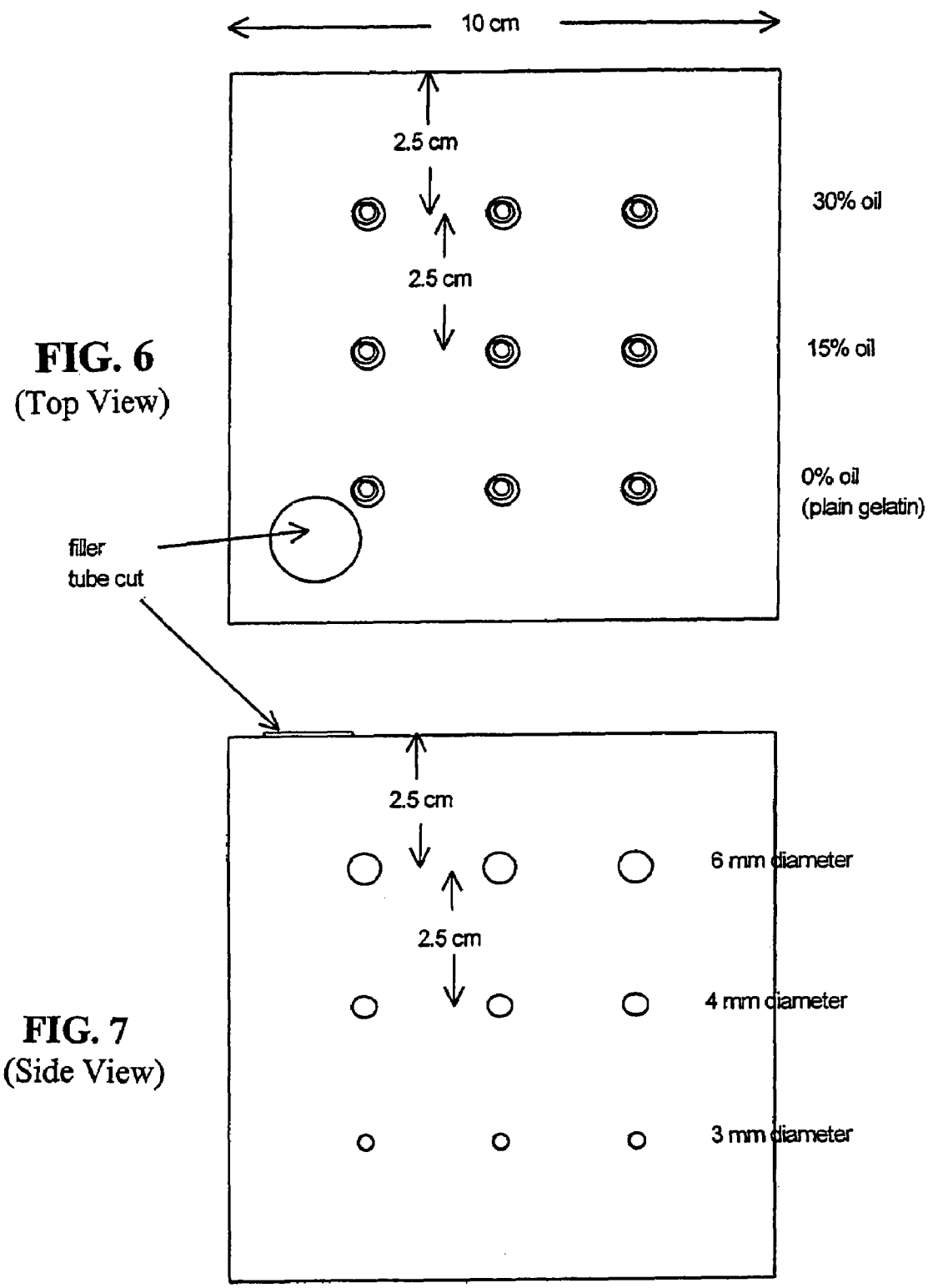
Top and side views showing the arrangement of spheres in Example 5 (spherical lesion phantom).

US 7,462,488 B2

TISSUE MIMICKING ELASTOGRAPHY PHANTOMS

CROSS-REFERENCE TO RELATED APPLICATION

This application is a divisional of application Ser. No. 10/265,293, filed Oct. 4, 2002, now abandoned, the disclosure of which is incorporated herein by reference.

STATEMENT OF GOVERNMENT INTEREST

This invention was made with United States government support awarded by the following agency: NIH Grant No. CA39224. The United States government has certain rights in this invention.

FIELD OF THE INVENTION

This invention pertains generally to materials for testing the perfomance of ultrasound and magnetic resonance elasticity imaging equipment.

BACKGROUND OF THE INVENTION

The early detection of cancer using medical imaging equipment requires the ability to detect small lesions or to delineate the boundaries of lesions that have properties close to those of the surrounding normal tissue. The measure of the smallest object visible with a given contrast is called the contrast detail resolution of the imaging system. Contrast-detail resolution and other performance tests of a medical imaging system are performed with objects called phantoms. A phantom with a variability of size and contrast objects is required for the evaluation of the contrast-detail resolution of the system. Such phantoms are commercially available for use with X-ray computed tomography, ultrasound imaging systems, and nuclear magnetic resonance imaging systems but are not generally available for the ultrasound and magnetic resonance elasticity imaging systems used in elastography. Elastography is a relatively recent technology directed at the early detection of tumors. Over the last decade, elastography has been recognized as having great potential as a tool for breast and prostate cancer diagnosis. In addition it may also play an important role in areas such as monitoring tumor ablation therapy and intravascular plaque classification. Presently, there is a great need for temporally stable heterogeneous phantoms to enable vigorous development and testing of elastographic hardware and software.

Elastography is the investigation of tissue elasticity using ultrasound methods. In ultrasound elastography (USE), an axial stress is applied to a tissue and the resulting strain of the tissue is determined from the change in the ultrasound echo signals before and after the application of the stress. With USE, a sample of tissue can be characterized by mapping out the local elastic strain of the analyzed tissue. The resulting mapping is called an elastogram. Hard tumor material will show less strain than softer tissues and this contrast between the elastic properties is picked up on an elastography image. The technique has the advantage of adding new diagnostic information to conventional ultrasound imaging.

Magnetic Resonance Elastography (MRE) is a particularly sensitive technique that couples the power of nuclear magnetic resonance imaging with the complementing information of elastography. There are two primary forms of MRE, harmonic MRE and quasistatic MRE. In harmonic MRE tissues are exposed to a deforming force at a frequency of 50-1000 Hz, generating longitudinal and shear waves throughout the tissue. In this method, an oscillating magnetic field gradient is used to induce spin phase change in proportion to the amplitude of the tissue motion. The tissue motion, or deformation, is measured by use of a phase contrast magnetic resonance technique and displayed in the form of an image. The quasistatic technique uses very low deformation frequencies between 0 and 1 Hz. In this method, wave propagation can be assumed to be negligible, with the tissue in an approximate state of static stress.

In addition to mimicking the elastic properties of soft tissue, the ideal tissue mimicking material for use in USE should have the same ranges of speeds of sound, attenuation coefficients, and backscatter coefficients as soft tissue. These parameters should be controllable in the manufacturing process of the phantom material, and their variation within the range of room temperatures should be small. Speeds of sound in human soft tissues vary over a fairly small range with an average value of about 1540 m/s. The speed of sound in fat is thought to be about 1470 m/s. The amplitude attenuation coefficients appear to vary over the range from 0.4 dB/cm to about 2 dB/cm at a frequency of 1 MHz in these tissues. The frequency dependencies of the attenuation coefficient of some soft tissues have been studied and, typically, it has been reported that the attenuation coefficient is approximately proportional to the ultrasonic frequency in the diagnostic frequency range of 1 to 10 MHz. An exception is breast fat, in which the attenuation coefficient is proportional to the frequency to the 1.7 power. This is discussed in F. T. D'Astous and F. S. Foster, "Frequency Dependence of Attenuation and Backscatter in Breast Tissue," Ultrasound in Med. & Biol., Vol. 12, pp. 795-808 (1986).

For use in elastography, the tissue mimicking materials must exhibit the same Young's modulus as that of the tissue being mimicked. The Young's modulus varies significantly from tissue to tissue. Krouskop et al., have reported in vitro values for the Young's moduli (E) for normal and abnormal breast and prostate tissues using precompression and low frequency superimposed sinusoidal loading. At 5% precompression in breast and 4% in prostate cases, E ranged from 18±7 kPa for breast fat through 241±28 kPa for prostate cancer. The Young's modulus for normal breast glandular tissue was found to be approximately 30 kPa and the Young's modulus for invasive and infiltrating ductal carcinoma was around 100 kPa.

Phantoms for use in MRE should also possess nuclear magnetic resonance properties reflective of those found in human soft tissues. Soft tissues exhibit T1's ranging from about 200 milliseconds (ms) to about 1200 ms and T2's from about 40 ms to about 200 ms. Typical values for the ratio T1/T2 lie between about 4 and about 10 for soft tissues. For a given soft tissue parenchyma, T1 in particular can exhibit a significant dependence on frequency as well as temperature.

Each of the above-mentioned parameters should be controlled in order to provide the desired range of values in the manufacturing process of the phantom, and should agree at all frequencies in the clinical ultrasound range of 1-10 MHz. In addition, the materials should possess long-term stability over periods of months or years with respect to the elastic, ultrasound, and magnetic resonance properties, and with respect to geometries, such as inclusion size and shape. Moreover, if the phantom includes inclusions of materials within the surrounding matrix which have different elastic, ultrasound and magnetic resonance properties than the surrounding matrix, these inclusions must be stable over time in both size and shape and in physical and chemical properties.

Materials which have been proposed for use in elastography phantoms to mimic soft tissues include homogeneous gels of gelatin and homogeneous gels of agar. The gelatin phantoms typically include a paraldehyde or formaldehyde crosslinking agent. The Young's modulus values for such phantoms depend on the dry weight of agar or gelatin in the gels, and in the case of gelatin, on the concentration of the formaldehyde or paraldehyde used to crosslink the materials. Such phantoms have been in use as ultrasound phantoms for many years. These materials suffer from several drawbacks. First, homogeneous agar gels bond only weakly together, therefore an agar inclusion will not be strongly bonded to its agar surroundings in a phantom. In addition agar gels are brittle and fracture at modest strains. In contrast, homogeneous gelatin gels possess durable inclusions that bond well to gelatin surroundings. However, it is very difficult to produce stable elastic contrast in these phantoms because the inclusions and the surrounding materials are made from gelatin having varying dry weight concentrations of gelatin and formaldehyde, and there is a strong tendency for the materials to approach a uniform concentration of gelatin and formaldehyde over time through diffusion. In addition, gelatins cannot be made to possess adequately large T1/T2 ratios to simulate soft tissues.

Another phantom that has been proposed for use in elastography imaging systems is a heterogeneous phantom having a gelatin section and an agar component. Unfortunately, the Young's modulus for the agar component in such phantoms was found to increase by a factor of 6 for strains between about 2% and 7%. It has been found that the Young's moduli of normal fat, breast and prostate parenchyma exhibit only a small dependence on strain over similar strain ranges. Thus, for strains of less than about 10%, it does not appear that agar by itself is a suitable material for mimicking normal breast or prostate tissue.

Polyvinyl alcohol gels have also been investigated regarding their suitability for magnetic resonance elastography phantoms. However, these materials do not possess long-term stability and are significantly stiffer than biological soft tissue.

Silicone rubber has also been tested for use with magnetic resonance elastography. Unfortunately, the speed of propagation of sound in silicone rubber is too low for this material to be a realistic option for ultrasound elastography studies.

Other phantoms for use in elastography include phantoms made from mixtures of agar and gelatin. One such phantom is made from 8% gelatin and between 1 and 3% agar, based on the dry weight of the materials, in the absence of a crosslinking agent. The Young's moduli of these materials are significantly temperature dependent at temperatures between 5° C. and 40° C. and the materials do not possess long-term stability with respect to shape and physical properties.

A phantom of this type is described in U.S. Pat. No. 5,312,755 to Madsen et al. This patent discloses a tissue mimicking NMR phantom that utilizes a base tissue mimicking material which is a gel solidified from a mixture of animal hide gelatin, agar, water and glycerol. The amount of glycerol can be used to control the T1. The preferred base material included a mixture of agar, animal hide gelatin, distilled water (preferably deionized), glycerol, n-propyl alcohol, formaldehyde, and p-methylbenzoic acid. The contrast-detail resolution phantom could include inclusions which have NMR properties which differ from the base tissue mimicking material. Differences in contrast between the surrounding base material and the spherical inclusions could also be obtained by the use of a solid such as powdered nylon added to the base material and the inclusions that has little NMR response but displaces some of the gelatin solution, decreasing the apparent $^1$H density to the NMR instrument.

Phantom materials composed of water based agar gels doped with $MnCl_2$ to control T1 for use in conventional magnetic resonance imaging systems have been reported. R. Mathur-DeVre, et. al., "The Use of Agar as a Basic Reference for Calibrating Relaxation Times and Imaging Parameters," Magn. Reson. Med., Vol. 2, 1985, p. 176. Agar gels doped with $CuSO_4$ have also been reported. M. D. Mitchell, et al., "Agarose as a Tissue-Equivalent Phantom Material for NMR Imaging," Magn. Reson. Imag., Vol. 4, 1986, p. 263.

A phantom material consisting of mixtures of agar gel and animal hide gel in which $CuSO_4$ was used to lower T1 for use in conventional magnetic resonance imaging has also been reported. Unfortunately, a long-term instability manifested itself in that a steady, very slow rise in T1 was observed over a period of months. This instability precludes the use of this material in magnetic resonance phantoms. The rise in T1 was perhaps due to the slow formation of metal-organic complexes, removing the $Cu^{++}$ paramagnetic ions. See J. C. Blechinger et al., "NMR Properties for Tissue-Like Gel Mixtures for Use as Reference Standards or in Phantoms," *Med. Phys.*, Vol. 12, 1985, p. 516 (Abstract). More recently, the problem of gradual increase in T1 in the agar, animal hide gel, $Cu^{++}SO_4^{--}$ gel has been eliminated by addition of the chelating agent EDTA (ethylenediaminetetraacetic acid). This stable material is excellent for use in MRI phantoms. See J. R. Rice, et al., "Anthropomorphic $^1$H MRS Head Phantom," *Med. Phys.*, Vol. 25, 1998, pp. 1145-1156.

Further ultrasound and MRI phantoms are illustrated in U.S. Pat. Nos. 6,238,343 and 6,318,146.

SUMMARY OF THE INVENTION

The present invention provides heterogeneous tissue mimicking phantoms for use in the testing and development of elastography imaging systems. In accordance with the invention, a tissue mimicking material is provided for imaging phantoms that can be used with ultrasound elastography and magnetic resonance elastography. The tissue mimicking material may be adjusted to appropriately mimic human tissue for particular normal tissues including organs, skeletal muscle, and fat. Abnormal tissues such as cancer and fibroadenomas can also be represented. The materials mimicking the various tissues may be incorporated in direct contact with one another in an imaging phantom and remain stable in their elastography imaging properties over time, allowing such phantoms to be used for long-term calibration and evaluation of the imaging instruments. Phantoms in accordance with the invention have particular application in simulating normal and abnormal breast and prostate tissue which is surrounded by and adjacent to muscle and fat tissue.

As used herein, the phrase "tissue mimicking material" refers to any material having elastic, ultrasound, and/or magnetic resonance properties that are sufficiently similar to the elastic, ultrasound, and/or magnetic resonance properties of real soft tissues to produce elastograms having an elastic contrast that allows the performance of the elastography imaging equipment to be qualitatively or quantitatively evaluated. The primary elastic properties of interest are the Young's modulus of the material and the elastic contrast between different materials. In a preferred embodiment, a tissue mimicking phantom will be made of materials having an elastic contrast that is within 20 percent, preferably within 10 percent, and more preferably within 5 percent of the real soft tissues being mimicked or modeled by the phantom.

The primary ultrasound properties of interest include the speed of sound in the materials and the attenuation and backscattering coefficients of the materials. In various preferred embodiments, the speed of sound in the materials in the phantoms will be within 25 percent, preferably 20 percent, and more preferably 10 percent of the speed of sound in the real soft tissues being mimicked or modeled.

The primary magnetic resonance properties of interest are the T1 and T2 values and the T1/T2 ratios of the materials. In various preferred embodiments the T1 and T2 values of the phantom materials will be within 25 percent, preferably within 20 percent, and more preferably within 10 percent of the T1 and T2 values of the real soft tissues being mimicked or modeled.

In accordance with one aspect of the present invention, a tissue mimicking phantom includes an elastography phantom container with a base tissue mimicking material therein made from an oil dispersed throughout a gel matrix formed from a gel-forming material and at least one inclusion which is at least partially embedded in the base material. The inclusion is also formed from a gel-forming material, preferably the same gel-forming material found in the base material. The inclusion gel may also have an oil dispersed in it, usually at a different concentration than in the base material. In this embodiment the elastic properties, and the Young's modulus in particular, of the tissue mimicking base material and the inclusion material are different, giving rise to an elastic contrast in the phantom, where elastic contrast is simply the ratio of the Young's modulus of the inclusion to the Young's modulus of the base, or background material. The gel-forming material in the base material and in the inclusion may comprise a gelatin or a mixture of agar and gelatin. The gel-forming material in the inclusion may comprise a homogeneous congealed gelatin or agar/gelatin mixture. In various embodiments, microscopic solid particles are dispersed throughout the base material and/or the inclusion to create soft tissue-like ultrasound attenuation coefficients. Powdered graphite, powdered nylon, concentrated bovine milk, and glass or plastic beads having a diameter of less than 40 micrometers (μm), and preferably less than 25 μm can be used to vary the attenuation coefficients of the phantom materials. In addition, larger solid particles (greater then 30 μm diameter) may be dispersed in either the base or the inclusion material to create soft tissue-like ultrasound backscattering. Glass or plastic beads and powdered nylon may be used to enhanced ultrasound backscatter.

Preferred inclusions are spherical or cylindrical in form and may be arranged so that several inclusions which span a range of diameters down to the smallest diameter which may generally be imaged by ultrasound or magnetic resonance elastography imaging apparatus are provided (e.g., from several centimeters to a minimum size in the range of 1 millimeter).

Enhanced dimensional and elastic stability can be achieved for a phantom when the chemical composition of the gel-forming material in the gel matrix of the base material and the gel-forming material in the inclusion are the same material. This prevents the diffusion of solvents and solutes between the base material and the inclusion, resulting in a heterogeneous phantom having ultrasound, elastic, magnetic resonance, and shape characteristics that do not change over long times.

Where the phantom is to be used in MRE studies, a mixture of a copper salt and a chelating agent for binding the copper ions of the salt may be added to the gel forming material in the base and/or the inclusion to produce a more tissue-like T1 value. A preferred copper salt is $CuCl_2$ and a preferred chelating agent is ethylenediaminetetraacetic acid (EDTA).

The tissue mimicking base materials and inclusions of this invention can be made to have Young's moduli, attenuation coefficients, backscattering coefficients, and speeds of sound which reflect the ranges found in normal and abnormal soft tissues. Some of the materials of the present invention are elastically linear for strains of up to 10%, that is, the Young's moduli for the materials are constant for strains of up to 10%. Heterogeneous phantoms made from these materials produce elastic contrast values between approximately 1 and 4, preferably between 1 and 3, which reflects the range of elastic contrast for actual tumors in soft tissue. In addition, the materials can be produced with hydrogen T1/T2 ratios, as well as T1 and T2 values, which span the ranges found in normal and abnormal soft tissues. The frequency dependence of US attenuation coefficients found for these materials also simulates that found in nonfat type soft tissues, and the materials exhibit long term stability in their elastic, ultrasound, and magnetic resonance properties. These materials do not shrink or extrude solution at their boundaries, and therefore are satisfactory for the construction of complex phantoms.

Another aspect of the invention provides a mesh-based tissue mimicking material comprising an open cell reticulated mesh material having a gel-forming material suffused throughout its interstices. These materials have a higher Young's modulus than materials made from a homogenous congealed gelatin. Examples of suitable mesh materials include polymer meshes, such as polyurethane and polyether meshes, having between about 10 and about 30 cells per inch. The gel-forming material may comprise a gelatin or a mixture of agar and gelatin. In a preferred embodiment the gel-forming material is made of pure agar. Agar is elastically nonlinear over strains of up to at least 10%. Therefore, these materials can be used as inclusions in a heterogeneous phantom to simulate tumors which exhibit nonlinear elasticity. The gel-forming material suffused within the mesh may take the form of a double layer of gel-forming material comprising an inner volume of agar and an outer shell of a gelatin-containing gel-forming material that surrounds the inner volume. The inner volume and outer shell may both be substantially spherical in shape, or the inner volume may be substantially spherical with an outer shell having spicules extending therefrom to simulate spiculated tumors.

The invention further provides a tissue mimicking phantom having a phantom container defining an interior space with a base material therein comprising a gel-forming material at least partially surrounding at least one mesh-based inclusion of the type described above. The gel-forming material of the base may comprise gelatin or a mixture of agar and gelatin. In addition, the gel-forming material of the base and/or the inclusion may contain a crosslinking agent. In a preferred embodiment, both the base and the inclusion contain gelatin and a crosslinking agent such that crosslinks may be formed between the gelatin of the base and the gelatin of the inclusion, preventing slipping at the base-inclusion boundary.

Yet another aspect of the invention provides a tissue mimicking material composed of millimeter (mm) sized agar spheres suspended in a crosslinked gelatin matrix. Agar is itself elastically nonlinear over strain ranges typically encountered in elastography studies. Therefore, a tissue mimicking material containing pure agar spheres surrounded by gelatin provides a good representation of elastically nonlinear tissues and tumors. The agar spheres are preferably closely packed within the gelatin, exhibiting a volume fraction of at least 30 percent, preferably at least 50 percent, more preferably at least 70 percent, and most preferably at least 75 percent of the material. The agar spheres are made from a mixture of agar powder and water. In a preferred embodiment the agar will be present in an amount of less than 2 weight percent of the mixture, based on the dry weight of the agar.

Further objects, features, and advantages of the invention will be apparent from the following detailed description when taken in conjunction with the accompanying drawings.

BRIEF DESCRIPTION OF THE DRAWINGS

In the drawings:

FIG. 6 is a top view of the phantom described in Example 5. The spheres containing 30% oil provide the lowest elastic contrast and the spheres containing 0% oil provide the highest elastic contrast.

FIG. 7. is a side view of the phantom described in Example 5.

DETAILED DESCRIPTION OF THE INVENTION

Figure 1:
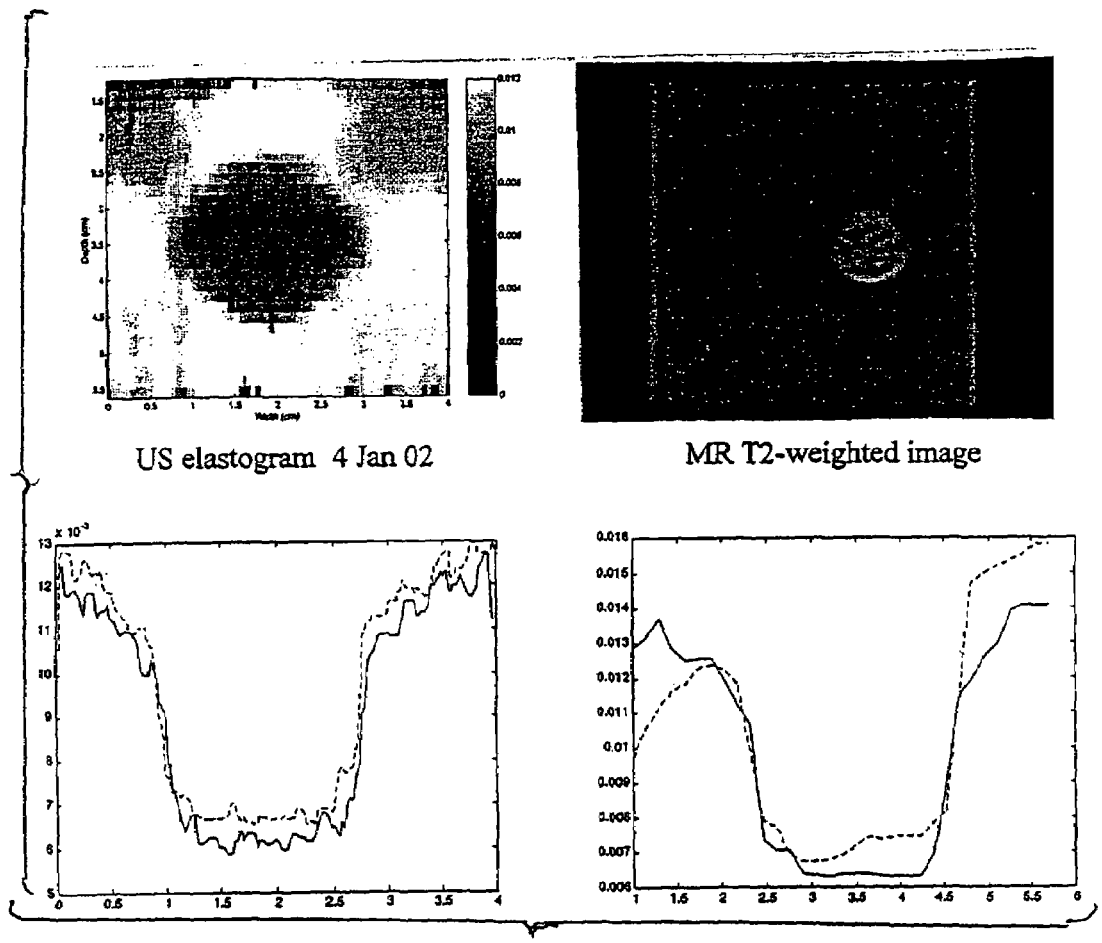
FIG. 1 shows an ultrasound elastogram (left) and a magnetic resonance elastogram (right) for a phantom composed of a 50% oil-in-gelatin base material and a gelatin inclusion. Also shown are the lateral (left) and axial (right) strain profiles for the elastograms taken on two different days (Jan. 4, 2002 (solid), and Jan. 15, 2002 (dashed)). The vertical axis in the strain profiles represents strain and the horizontal axis represents centimeters.

The present invention provides tissue mimicking materials and heterogeneous phantoms for use in the testing and development of elastography imaging systems. The phantoms of the present invention provide long term stability in terms of both shape and elastic and magnetic resonance properties. This is very important because remaking phantoms as they deteriorate is costly in terms of time and money, particularly because the characterizing parameters (Young's modulus, ultrasound propagation speed, ultrasound attenuation coefficients, elastic contrast, and the two magnetic resonance relaxation times) need to be redetermined for each new phantom.

The materials of the present invention can be designed to closely mimic the elasticity characteristics of soft tissue. In particular, the phantom materials possess Young's moduli of between about 10 and about 300 kPa, preferably between about 10 and about 270 kPa, and more preferably between about 30 and about 100 kPa, at 5% precompression. The elastic contrast for the various materials in the phantoms may typically be between about 1 and about 4 and preferably between about 1 and about 3. In addition, the speed of sound propagation in the materials ranges from 1300 m/s to 1650 m/s at room temperature (i.e., about 22° C.) which mimics the speed of sound in various fat, non-fat, and tumor tissues. The materials also possess attenuation coefficients of between about 0.1 dB/cm/MHz and about 2.0 dB/cm/MHz, which includes the attenuation coefficients from fat (0.4 dB/cm/MHz) through muscle (1.5 dB/cm/MHz). In the case of materials for use in magnetic resonance elastography, the hydrogen density and relaxation times (T1 and T2) of the materials can be made to reflect those of several types of tissues. For examples, T1's ranging from about 200 milliseconds (ms) to 1200 ms and T2's from about 40 ms to 200 ms can be produced in the materials, with values for the ratio T1/T2 between 4 and 10.

One aspect of the invention provides a tissue mimicking phantom material composed of a base material made from an oil dispersed in a gel-forming material and at least one inclusion suspended in and in contact with the base material. The inclusion is itself composed of a gel-forming material, preferably the same gel-forming material used to form the base material. The inclusion material could also contain oil dispersed in it at a different concentration than in the background material. In a preferred embodiment, the gel-forming material is a gel solidified from gelatin, such as animal hide gelatin, or a mixture of gelatin and agar. The oil is preferably safflower oil, but may be olive oil, castor oil, or kerosene. The hardness of the base and inclusion materials can be adjusted by changing the percent oil in the dispersion. The gel-forming materials of the invention are crosslinked by adding suitable crosslinking agents, such as paraaldehyde or formaldehyde, to the gel-forming material during the congealing process, described in more detail below.

The tissue mimicking base and inclusion materials may contain solid scattering particles dispersed throughout the gel-forming material to increase backscattering and attenuation to levels that are reflective of backscattering and attenuation levels in various types of normal and abnormal soft tissue. The use of such particles allows a wide range of scattering and attenuation levels to be achieved. Suitable solid particles for increasing attenuation include powdered graphite, powdered nylon, and glass or plastic beads, having a mean diameter of less than 20 μm. Concentrated bovine milk can also be added to increase attenuation. The scattering particles should be large enough to induce scattering and spaced sufficiently close to each other that an ultrasound scanner is incapable of resolving individual scattering particles. Powdered nylon and glass or plastic beads having a mean diameter of greater than 30 μm may be used to enhance backscattering. The addition of scattering particles is particularly useful for simulating muscle tissue. If glass or plastic beads are used, they should be selected and treated to have a low effect on the relaxation (T1 and T2) properties of the tissue mimicking materials. For example, glass beads may be treated by soaking them in nitric acid to clean the surfaces thereof to reduce the effect of any surface contamination on the magnetic resonance properties.

In order to optimize the ultrasound and/or the magnetic resonance characteristics of the materials for use as tissue mimicking phantoms, organic hydroxy compounds may be added to the gel-forming materials in order to increase the speed of sound to levels similar to those found in soft tissue and to lower T1 to a value in the range of T1 values found in soft tissues. This is particularly advantageous for oil-in-gelatin dispersions which tend to have a lower speed of sound than real soft tissue. Organic hydroxy compounds that may be used to alter the speed of sound in gel-based emulsions are well known in the art. Examples of such compounds include, but are not limited to, n-propanol, glycerol, ethanol, and ethylene glycol. Glycerol is particularly suitable because, in addition to increasing the speed of sound in the material, the glycerol content can be varied to control the value of T1 independently of T2, since the glycerol to water ratio has little effect on the T2 value of the material. Glycerol is also insoluble in oil which is advantageous because the phantoms are typically stored in vegetable oil. Thus, this tissue mimicking material can be produced in the proper mixture of components to have T1/T2 ratios, as well as T1 and T2 values, which span the ranges found in normal and abnormal soft tissues. The frequency dependence of T1 and T2 in the tissue mimicking material simulates that found in nonfat type soft tissues, and the material exhibits long term stability of the T1 and T2 values. An inorganic salt, such as NaCl, can also be added to increase the ultrasonic speed. Such a material also has the advantage that it is insoluble in the vegetable oil in which the phantoms may be stored.

For tissue mimicking materials that are designed for use with MRE imagers it is desirable to add a $Cu^{++}$ copper salt and a chelating agent into the gel-forming material in order to lower the T1 value to a soft tissue-like value. The use of a copper salt and chelating agent to lower T1 may be utilized as described in J. R. Rice, et al., "Anthropomorphic $^1H$ MRS Head Phantom," *Medical Physics*, Vol. 25, 1998, pp. 1145-1156. An appropriate chelating agent is EDTA. EDTA binds to the $Cu^{++}$ and prevents imobilization of the $Cu^{++}$ through the formation of metal-organic complexes with the rigid agarose or other gel that may be used. Thus, the use of $CuCl_2$ and EDTA together, forming mobile paramagnetic particles, results in a stable T1.

In addition, the gel-forming materials in the tissue mimicking materials may include components which stabilize the material against attack by micro-organisms, particularly bacterial attack. For example, n-propanol, formaldehyde, p-methylbenzoic acid, and thimerosal (the sodium salt of ethylmercurithiosalicyclic acid) can be utilized to prevent bacterial invasion, with the formaldehyde also functioning as a crosslinking agent for the gelatin molecules.

In one preferred embodiment of the invention the base material comprises a 50% (volume percent) safflower oil-in-calfskin gelatin dispersion and the inclusion comprises a homogeneous congealed calfskin gelatin. In both the base and the inclusion, the gelatin comprises a mixture of calfskin gelatin, thimerosal, glass beads (22 μm diameter), and formalin (a formaldehyde solution) which serves to crosslink the gelatin. The bead concentration in the materials was approximately 4 grams of 3000 E Potters beads (Potters Industries, Valley Forge, Pa.) per liter.

In another preferred embodiment of the invention the base material comprises a 32% (volume percent) safflower oil-in-calfskin gelatin dispersion and the inclusion comprises a powdered graphite-in-calfskin gelatin dispersion. In both the base and the inclusion, the gelatin comprises a mixture of calfskin gelatin, thimerosal, glass beads (22 μm diameter) and formalin. The bead concentration in the materials was approximately 4 grams of 3000 E Potters beads (Potters Industries, Valley Forge, Pa.) per liter.

In yet another preferred embodiment of the invention, the base material comprises a 50% (volume percent) safflower oil-in-agarose gelatin dispersion and the inclusion comprises a homogeneous congealed agarose gelatin. In both the base and the inclusion the agarose gelatin comprises an aqueous mixture of agar, calfskin gelatin, thimerosal, glass beads (22 μm diameter), $CuCl_2$ and EDTA. The $CuCl_2$ and EDTA are present to lower the T1 value of the material.

The following is an exemplary general technique for producing a typical phantom tissue mimicking material having a gelatin inclusion embedded in an oil-in-gelatin base material according to the present invention. First, an aqueous molten gelatin for incorporation into an inclusion is formed by combining a dry gelatin powder with distilled water. The mixture is heated at a temperature and for a time sufficient to clarify the solution. Optionally, a small amount of preservative, an organic hydroxy compound, a copper salt and a chelating agent, and microscopic attenuating particles and/or scattering particles may be added to the mixture in order to produce more tissue-like elastic, ultrasound, and magnetic resonance properties. The gelatin and any additives are mixed well, being careful not to introduce any air into the mixture. The mixture is allowed to cool and an amount of crosslinking agent sufficient to crosslink the gelatin is added to the mixture, typically between about 5 and about 15 ml per liter of the gelatin mixture of formalin will be sufficient for this purpose.

The amount of organic hydroxy compound added to the mixture should be sufficient to raise the speed of sound in the material to a tissue-like value. The actual amount required will vary depending on the nature of the hydroxy compound and the type of tissue to be simulated, however, for a typical oil-in-gelatin dispersion the mixture will contain between about 60 ml and about 100 ml of n-propanol per liter of material. Similarly, the amount of attenuating and/or scattering particles added should be sufficient to increase the ultrasound attenuation and scattering to a range that is representative of soft tissue. Again, the amount required to achieve this will vary depending upon the nature of the particles and the characteristics of the type of tissue to be simulated, however, for a typical gelatin inclusion, between about 20 and about 100 grams of attenuating particles and between about 1 and about 8 grams of scattering particles should be added per liter of mixture.

If a copper salt and a chelating agent are included in the gelatin mixture the amount added should be based on the desired T1 value of the tissue to be simulated. Typically, the copper salt will be $CuCl_2.2H_2O$ and will be present in an amount between about 0.2 grams and about 1.8 grams per liter of gelatin solution. The chelating agent will typically be EDTA-tetrasodium salt hydrate (MW=380.2) in an amount between about 0.43 grams and about 3.9 grams per liter of gelatin solution.

Next the mixture is poured into a mold. The mold is then sealed, placed under positive pressure, and rotated about a horizontal axis at a rate and for a time sufficient to congeal the gel-forming material without sedimentation of any attenuating or scattering particles. The molds are typically two part acrylic molds held together with holes and pegs to produce an exact alignment. The molds may be coated with a thin layer of petrolatum to prevent sticking and facilitate removal of the congealed inclusion. Such molds can be used to produce spherical or irregularly shaped three dimensional simulated tumors.

A typical tissue mimicking oil-in-gelatin base material, in accordance with the present invention, may be made according to the following steps. First, an aqueous molten gelatin is formed substantially as described above for the inclusion, with the exception that an oil is now added to the gelatin mixture, along with any preservatives, organic hydroxy compounds, copper salts, chelating agents, or scattering and attenuating particles. The amount of oil added should be sufficient to provide a dispersion having elasticity, ultrasound, and magnetic resonance characteristics that reflect those found in soft tissues. A higher percent of oil in the dispersion produces a less stiff material having a lower Young's modulus. The amount of oil required will depend on the Young's modulus desired. However, for a typical oil-in-gelatin emulsion the volume percent of the oil in the dispersion is preferably between about 20 and about 60 volume percent. A surfactant is added to facilitate dispersion of the oil into sufficiently small droplets that they are not visible to the naked eye (typically less than about 30 μm in diameter). Typically, 7.5 cc of liquid Ultra Ivory®), produced by the Proctor and Gamble Company, is sufficient for adequate emulsification. The gelatin, oil, and any attenuating or scattering particles are mixed well, being careful not to introduce any air into the mixture, to produce an oil-in-gelatin dispersion. The mixture is allowed to cool and an amount of crosslinking agent sufficient to crosslink the gelatin is added to the mixture.

Once the congealed inclusions and the molten oil-in-gelatin dispersion have been formed, the inclusions are embedded in the base material such that the inclusions and the base material are in direct contact and are bonded to one another. This can be accomplished by removing the congealed inclusions from their molds and suspending them with stainless steel wire (0.1 or 0.3 mm) in larger, usually one-piece, molds and pouring the molten oil-in-gelatin dispersion into the larger mold such that it surrounds or partially surrounds the inclusion. The wires may be covered with a thin layer of petrolatum to facilitate withdrawal once the base material is congealed around the inclusions. The larger mold is then sealed, placed under positive gauge pressure, and rotated at a rate and for a time sufficient to congeal the gel-forming material without sedimentation of the oil or any attenuating/scattering particles. After the base material has been congealed, the mold is placed in an oven at about 50° C. for a time sufficient to hasten the completion of crosslinking of the gelatin by the crosslinking agent (typically at least 3 days). Without baking, crosslinking is typically completed within one month.

Although the baking process likely aids in crosslinking completion, the most dramatic effect is the lowering of the Young's modulus. In fact, it is the latter effect that is likely the most important and useful in that the ranges of Young's moduli available is broadened and lowered, to produce materials that are suitable for use in testing elastography images. This effect is illustrated in Example 6 below.

Alternatively, phantoms having cylindrical inclusions can be formed by first pouring the molten oil-in-gelatin material described above into a mold, which will typically be a square or rectangular mold, containing a stainless steel cylinder and allowing the base material to congeal around the cylinder. Once the base material is congealed and the crosslinking reaction has increased the melting temperature of the material to at least 60° C., the cylinder is removed and the molten gelatin inclusion material is poured into the resulting cylindrical opening and allowed to congeal. The mold is placed in an oven at about 50° C. for a time sufficient to assure complete crosslinking of the gelatin by the crosslinking agent (typically at least 3 days).

Phantoms containing an agar/gelatin inclusion surrounded by oil-in-agar/gelatin base material are made substantially as described above, with the exception that the molten gel starting material that goes into both the inclusion and the base material is formed by combining molten aqueous agar with molten aqueous gelatin. The dry weight percent agar will vary depending on the desired hardness of the material, however, for a typical phantom according to the present invention, the mixture will contain between about 1.0 and about 5 percent agar and between about 3 and about 10 percent gelatin, based on the dry weight of the materials. This includes embodiments wherein the mixture contains between about 1.2 and about 4.3 percent agar and between about 3.9 and about 8.0 percent gelatin based on the dry weight of the materials.

A second aspect of the invention provides a tissue mimicking material made from a gel-forming material suffused throughout the interstices of an open-cell reticulated mesh material. These materials may take on a variety of shapes, but preferred shapes include spheres and cylinders. The mesh material is preferably a polymeric mesh having between about 10 and about 30 cells per inch. Examples of suitable mesh materials include polyurethane and polyether meshes. The gel-forming material may be gelatin, including animal skin gelatin, or a mixture of agar and gelatin. These materials may be crosslinked by adding a crosslinking agent to the gel-forming material during the congealing process. Suitable crosslinking agents have been described in more detail above. The gel-forming material may also be pure agar. Because agar exhibits a nonlinear elasticity over strain ranges typically used in elastography studies (i.e. strains of up to at least 10%) using agar as the gel-forming material provides a material that is more representative of those cancers which possess non-linear elasticities.

The tissue mimicking material of this aspect of the invention may have a double layered structure wherein an inner volume of gel-forming material is suffused into an interior portion of the mesh material and an outer shell of gel-forming material is suffused into the mesh material around the inner volume, such that the outer shell is in contact with and partially or completely surrounds the inner volume. Preferably, the inner volume is comprised of pure agar and the outer shell contains gelatin and a crosslinking agent. The inner volume and the outer shell are held together with the mesh to prevent slipping at the inner volume/outer shell interface. In one embodiment the mesh and the inner volume and outer shell are spherical. In another embodiment, the inner volume which is contained within an interior portion of the mesh material is substantially spherical in shape, while the outer portions of the mesh material and the outer shell gel-forming material suffused therein have spicule shaped arms extending outward from the center of the mesh material. This design mimics tumors, such as breast cancer tumors, which are frequently spiculated.

The mesh-based tissue mimicking materials above may be incorporated as inclusions into a tissue mimicking base material to form a heterogeneous phantom. In this phantom the inclusions are at least partially surrounded by a base material comprising a gel-forming material. The gel-forming material may comprise gelatin or a mixture of agar and gelatin and may be the same gel-forming material found in the inclusion. In a preferred embodiment both the base and the inclusion contain gelatin and the gelatin of the base and the gelatin of the inclusion are crosslinked. For such materials, there is no slipping at the inclusion/base material interface.

Optionally, the gel-forming base and inclusion materials may include additives designed to reproduce soft tissue-like elasticity, ultrasound, and magnetic resonance properties and to prolong the life of the phantom. These additives include solid scattering and attenuation particles dispersed throughout the gel-forming material to increase backscattering and attenuation levels. Other additives include organic hydroxy compounds or a copper salt and a chelating agent to lower the T1 value of the material. Optionally, the base or inclusion material may include a preservative which protects the material against bacterial attack. These types of additives have already been discussed in greater detail above.

A heterogeneous phantom containing a simulated spiculated tumor can be formed by imbedding the spiculated double layer material described above in a base material comprising a gelatin and a crosslinking agent. In a preferred embodiment, the inner volume of the double layer inclusion is composed of pure agar and simulates the elasticity, ultrasound, and magnetic resonance properties of an elastically nonlinear tumor, the outer shell contains gelatin and simulates the elasticity, ultrasound, and magnetic resonance properties of tumor spiculations, and the base material contains gelatin and simulates the elasticity, ultrasound, and magnetic resonance properties of normal tissues, such as fat and muscle.

Tissue mimicking materials composed of a single layer gel-forming material suffused within the interstices of a mesh material can be made according to the following general procedure. First a piece of mesh material is cut into the desired shape, typically a cylinder or a sphere, and placed into a mold. Next, a molten gel-forming material is formed. This material may be the same type, and may be made by the same process as the gel-forming material used to form the gelatin or agar/gelatin inclusions used in the oil-in-gelatin based phantoms described above. The molten material is poured into the mold containing the mesh material and allowed to infiltrate the pores. The material in the mold is then allowed to congeal. The congealing process is substantially the same process outlined above for the oil-in-gelatin based materials. Once the congealing process is complete, the mesh material which is now embedded in the gel-forming material is removed from the mold and the excess gel forming material is removed from the outside of the mesh either by trimming the material away or by immersing and swirling the embedded mesh in warm water until the excess gel-forming material melts away.

Tissue mimicking materials composed of a double layer gel-forming material suffused within the interstices of a mesh material can be made as follows. First a mesh material is cut into a desired shape. This may be a generally smooth sphere or it may be a sphere having outer spicules, or arms, extending outwardly therefrom. The material is placed into a mold. A first molten gel-forming material, which is preferably a pure agar solution is then prepared and poured into the mold and allowed to infiltrate the pores in the mesh material. The mold is sealed and the gel-forming material is allowed to congeal. The gel embedded mesh is removed from the mold and swirled in warm water until enough of the first gel-forming material has melted away to exposed the outer portions of the mesh material, producing a mesh having a central volume of gel-forming material. The mesh is then placed into a second mold and a second molten gel-forming material, which is different from the first material, is poured into the mold. The mold is sealed and the second gel-forming material is congealed around the first material to form a second outer shell of material around the first shell. Again, the second gel-forming material may be the same type, and may be made by the same process as the gel-forming material used to form the gelatin or agar/gelatin inclusions used in the oil-in-gelatin based phantoms described above.

Heterogeneous phantoms may be made from the above-described mesh-based materials by embedding them as inclusions into a base material such that the they are at least partially surrounded by base material. The base materials may contain gelatin or a mixture of agar and gelatin. In addition, the base materials may be comprised of oil-in-gelatin or oil-in-agar/gelatin dispersions of the type described above. The inclusions may be embedded in the base material by suspending the pre-formed inclusions in a large mold and pouring the base material, in a molten form, into the mold and congealing and crosslinking the base material, in a manner similar to that described above. Alternatively, phantoms having cylindrical inclusions can be formed by forming a congealed base with a cylindrical hole extending through it, inserting a cylinder mesh into the hole, filling the cylindrical hole around the mesh, and allowing any crosslinking reactions to be completed.

A third aspect of the invention provides a tissue mimicking material made from millimeter sized agar spheres suspended within a gelatin matrix. The agar spheres have a diameter of less than 5 mm, and preferably less than 3 mm and are closely packed within the gelatin matrix, accounting for at least 30 and preferably 70 volume percent of the material. The spheres are made from a mixture of agar powder and water. Preferably, the dry weight concentration of agar in the mixture is less than about 2 weight percent (70 grams per liter). For a more detailed description of these materials, see R. B. Chin et al, *Med. Phys.*, Vol. 17, pp. 380-390 (1990) and E. L. Madsen et al., *Med. Phys.*, Vol. 9, p. 703-710 (1982), both of which are incorporated by reference.

The materials of the present invention have a variety of practical applications, including the calibration, standardization and performance assessment of elastography machines and the various algorithms used to create elastograms. The phantoms may also be used to assess the accuracy and resolution of an elastography instrument. In addition, anthropomorphic phantoms can be made to simulate complex body structures, such as a breast or prostate, in which multiple types of tissue (fat, muscle, tumor, etc.) are in contact with each other. Such phantoms may be used to challenge elastography systems under development with a more realistic elastographic system. Finally, because the phantoms can be designed to be tissue mimicking materials for use in both ultrasound elastography and magnetic resonance elastography systems, the same phantom can be used for direct performance comparisons between the two modalities.

Figure 4:
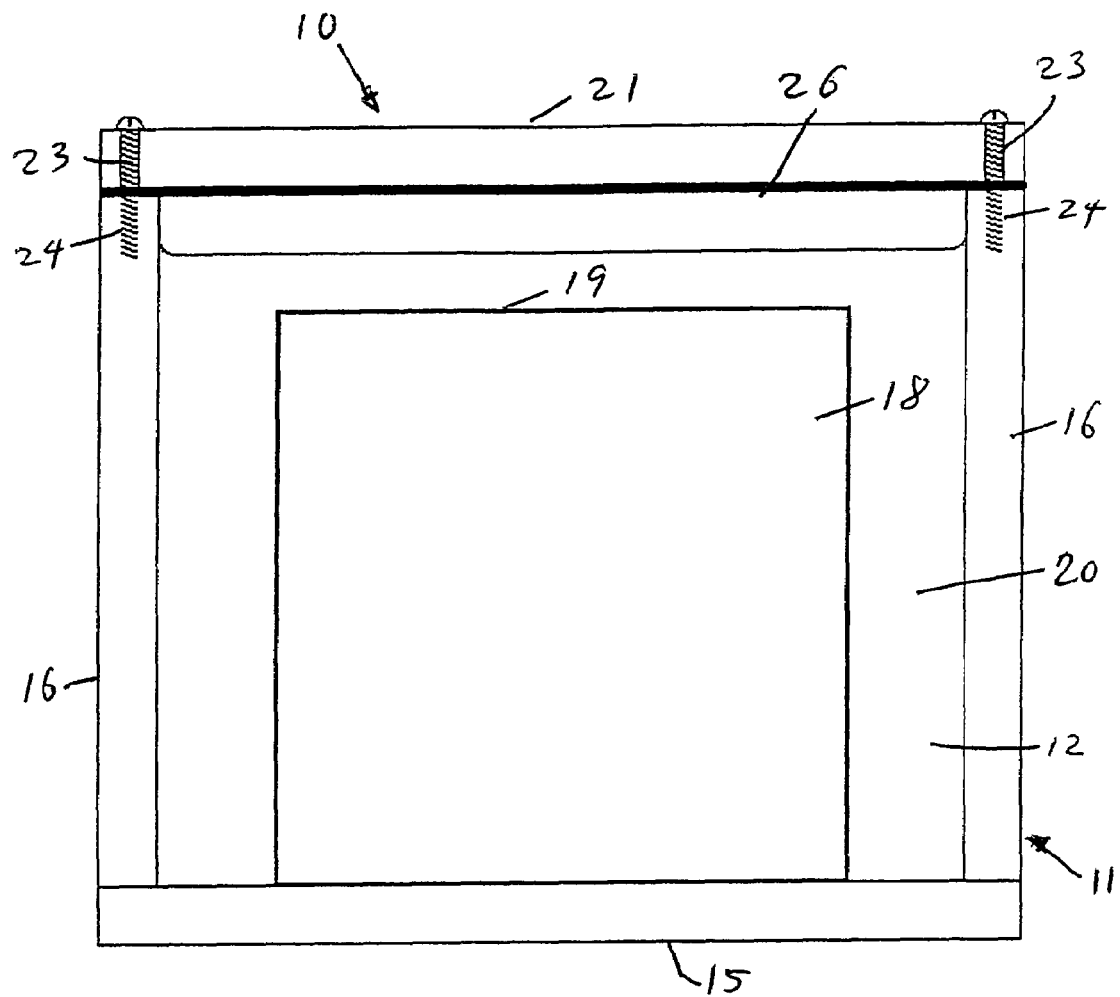
FIG. 4 is a side view of an exemplary elastography phantom in accordance with the invention.
Figure 5:
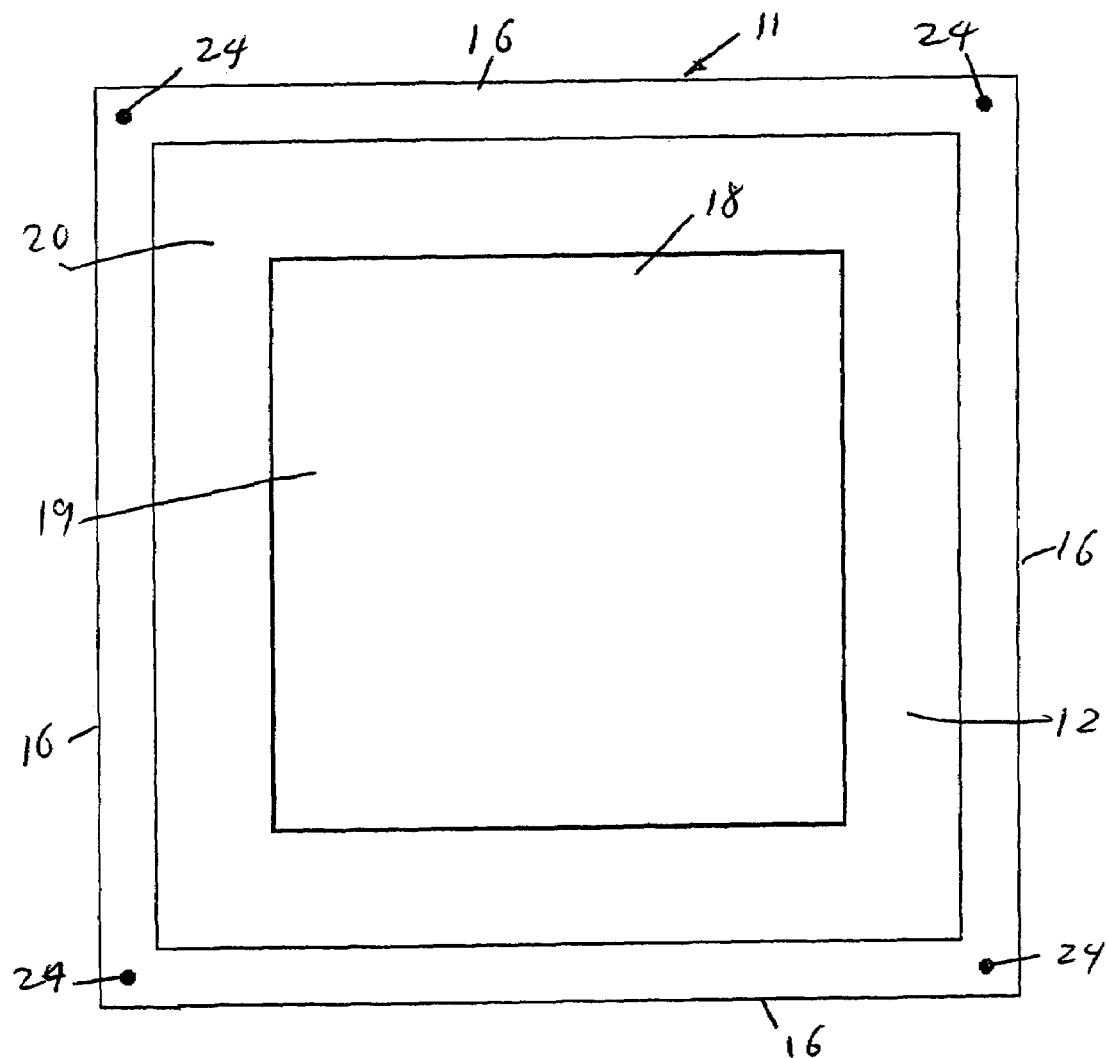
FIG. 5 is a top view of the elastography phantom of FIG. 4.

An exemplary elastography phantom that may be used for ultrasound or magnetic resonance elastography is shown generally at 10 in FIGS. 4 and 5. The phantom 10 includes a container 11 that encloses an interior space 12 in which tissue mimicking material may be held. The container 11 may have any desired geometrical shape. For illustrative purposes, the walls of the container 11 enclosing the interior space 12 include a bottom wall or base 15 and four side walls 16 that are joined to each other to define a generally rectangular interior space 12. The container walls 15 and 16 may be made of any material that is liquid tight, is preferably resistant to attack by the material held in the container, and does not interefere with ultrasound or MRI imaging, as appropriate. An example of a suitable material for the container walls 15 and 16 is acrylic plastic.

A block of tissue mimicking material 18 in accordance with the invention is supported on the bottom wall 15 within the interior space 12. The block of tissue mimicking material 18 is formed as described above, and may have the cubic form shown in FIGS. 4 and 5, although other geometries may also be utilized. The sides of the block of material 18 are preferably spaced from the side walls 16 to provide space for a surrounding bath of appropriate covering liquid 20, such as an oil (e.g., vegetable oil), which also covers the top surface 19 of the tissue mimicking material 18. The oil bath 20 is preferably utilized to help prevent evaporation of liquid from the tissue mimicking material 18. A cover 21 (e.g., also formed of acrylic) may be attached to the container 11 (such as by the screws 23 shown in FIG. 4 threaded into tapped holes 24 in the container walls 16). The cover 21 further helps to prevent loss of liquid from the material 18 (and a resilient gasket 26 may be used between the cover 21 and the side walls 16 to further seal the interior of the container).

To use the phantom 10, the cover 21 is removed and a (typically flat) applicator is used to apply stress to the top surface 19 of the tissue mimicking material 18. In the dynamic type of MRI or ultrasound imaging, the plate applies a sinusoidal shear or longitudinal stress, with a typical frequency of 60 Hz and an amplitude of 0.5 mm. In the quasi-static method for MRI or ultrasound, the plate compresses the tissue mimicking material 18 vertically (i.e., between the top surface 19 and the bottom wall 15). Other shapes may be used for the tissue mimicking material, including anthropomorphic shapes, if desired.

The phantoms of the present invention thus can be readily manufactured and are easy to use.

The production of tissue mimicking materials made from various gel-forming materials and having various gel proportions are illustrated in the non-limiting examples presented below.

EXAMPLES

Example 1

A heterogeneous phantom composed of a 50% oil-in-gelatin base material with a gelatin inclusion was made according to the following steps. First, 15.4 grams of dry weight 200 bloom calfskin gelatin (obtained from Vyse Gelatin Co.) was added to 100 ml of distilled water. The mixture was heated in a double boiler until it clarified at a temperature of about 90° C. Next, the mixture was cooled to 55° C., 1 gram of thimerosal per liter of mixture was added, and 50% by volume of safflower oil (also at 55° C.) was added to the mixture along with 1 ml of liquid detergent. The detergent reduces the surface tension, facilitating the formation of microscopic droplets during agitation. Enough glass beads were added to produce a mixture composed of 4 grams of glass beads per liter of mixture. The glass beads had a 22 μm mean diameter. The resulting mixture was mixed in a blender operated at low speed powered by a Variac power supply intermediary. After emulsification, the mixture was cooled to 36° C. and 7 ml of formalin solution (i.e., a 37% aqueous formaldehyde solution) per liter of the molten gelatin mixture was added. The mixture was then poured into a 9 cm×9 cm×9 cm square mold having a 2 cm diameter stainless steel cylinder extending through it. The mold was sealed, placed under positive gauge pressure, and rotated around a horizontal axis for 12 hours allowing the mixture to congeal fully. The stainless steel cylinder was then removed and a molten calfskin gelatin mixture was poured into the resulting cylindrical hole and allowed to congeal. The molten gelatin had the same composition and was produced in the same way as that which had been mixed with the safflower oil to produce the background material, including 1 gram per liter of thimersal. The molten gel also contained 4 grams per liter of 22 μm diameter glass beads as the background emulsion. The mold was then placed in an oven for 10 days at 55° C. to complete the crosslinking of the gelatin.

The background material mimics breast glandular tissue in terms of elasticity and ultrasound parameters. Also, the NMR T1 value was 495 ms which is a reasonable value mimicking breast glandular tissue.

FIG. 1 shows an ultrasound elastogram (gray-scale mapping of local elastic strains) (left) and a magnetic resonance electrogram (right) for the material of Example 1. The ultrasound elastogram was acquired with a 7.5 MHz scan head with a 60% band width on a model SSD-2000 Aloka scanner. The method for obtaining the ultrasound elastograms is described in Ophir, J. et al, "Elastography: a quantitative method for imaging the elasticity of biological tissues," *Ultrasonic Imaging*, Vol. 13, 1991, pp. 11-134, which is incorporated herein by reference. Briefly, an apparatus has a 10 cm×10 cm flat aluminum plate with the ultrasound transducer affixed so that the beam passes through a slot in the plate. The plate is parallel to a base on which the phantom sits. The phantom and plate are submersed in safflower oil. The plate is lowered to slightly compress the phantom and an ultrasound image is digitized. The plate is lowered to slightly again, compressing the phantom additionally by 1%, and a second ultrasound image obtained. Software then computes the local elastic strains by comparing the two images.

Ultrasound, elastic, and magnetic resonance properties of the materials are listed in Tables 1 and 2.

Example 2

A heterogeneous phantom composed of a 32% oil-in-gelatin base material with a graphite-in-gelatin inclusion was made according to the following steps.

The 32% oil-in-gelatin background emulsion material was made in the same manner as that in the phantom of Example 1, except that the volume percent safflower oil was 32% instead of 50% and the concentration of detergent was reduced by a factor of 32/50. This background emulsion also contained 4 grams per liter of 22 μm diameter glass beads.

The graphite-in-gelatin inclusions was made using the same molten gelatin formulation as that used in forming the background material but, instead of making an emulsion, 50 grams per liter of No. 9039 powdered graphite (Superior Graphite Co., Chicago, Ill.) was added. Four grams per liter of 22 μm diameter glass beads were also added.

Both background and inclusion contain 7 ml of formalin per liter of molten gelatin.

Figure 2:
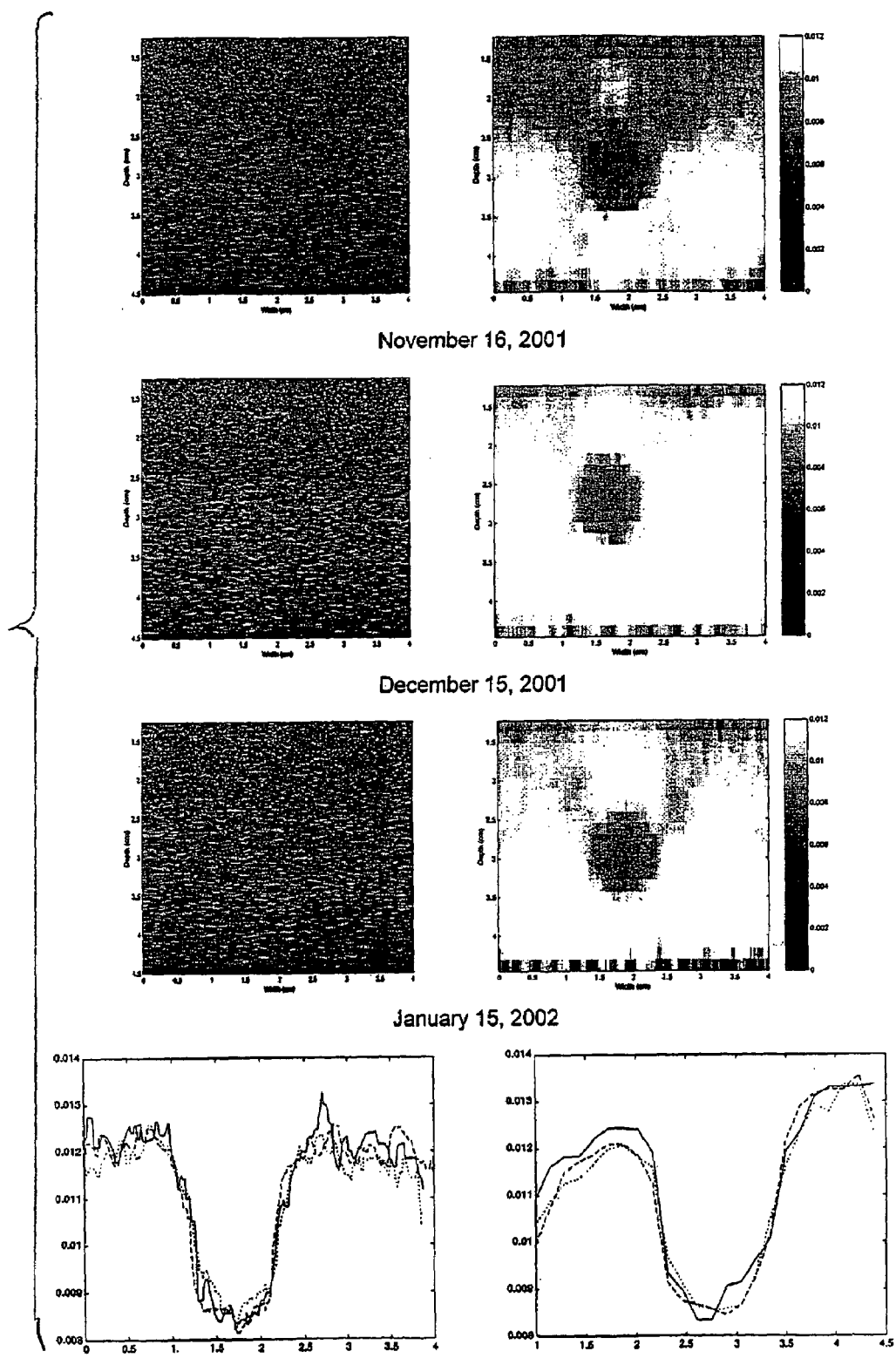
FIG. 2 shows ultrasound B-scan images (left) and elastograms (right) for a phantom composed of a 32% oil-in-gelatin base material and a graphite-in-gelatin inclusion. Images and elastograms were made 4 (top), 5 (center) and 6 (bottom) months after production of the phantom and demonstrate long-term geometrical stability. The corresponding lateral (left) and axial (right) elastic strain profiles for the elastograms demonstrating long-term stability of elastic properties are shown in the lower panels. The elastic strain profiles were taken on Nov. 16, 2001 (solid), and Dec. 15, 2001 (dashed). The vertical axis in the strain profiles represents strain and the horizontal axis represents centimeters.

FIG. 2 shows three ultrasound elastograms (right) for the material of Example 2, taken over a two-month period. The ultrasound elastograms were acquired with a 7.5 MHz scan head with a 60% band width on a model SSD-2000 Aloka scanner.

Ultrasound, elastic, and magnetic resonance properties of the materials are listed in Tables 1 and 2.

Example 3

A heterogeneous phantom composed of a 50% oil-in-agar/gelatin base material with an agar/gelatin inclusion was made according to the following steps.

A molten aqueous agar solution was produced consisting of 10.2 grams of dry agar and 500 cc of distilled water, and a molten gelatin solution was made with 42 grams of dry 200 bloom calfskin gelatin and 400 cc of distilled water. Both solutions were clarified at 90° C., then lowered to 55° C. Then 280 cc of the gelatin solution and 420 cc of the agar solution were mixed together at 55° C., followed by addition of 0.42 grams of $CuCl_2 \cdot 2H_2O$ (MW=170.5), 0.91 grams of the tetrasodium hydrate salt of EDTA (MW=380.2), 5.6 grams NaCl, and 0.7 grams of thimerosal.

To make the background emulsion, 600 cc of the 55° C. molten agar/gelatin solution described above were mixed with 600 cc of safflower oil, also at 55° C. Ten cc of detergent (Ivory Liquid®, Proctor and Gamble Co.) were then added and the mixture stirred vigorously to complete emulsification. The 1200 cc of mixture was cooled to 35° C. and 1.4 cc of formalin was added to the mixture. The resulting mixture was cooled to 28° C., poured into a cubic mold and rotated about a horizontal axis at 2 RPM for 12 hours during which time complete congealing occurred.

The cubic mold had a 2 cm diameter stainless steel cylinder extending through it, and that cylinder was withdrawn to allow introduction of the molten inclusion material. The method for making the inclusion material is given above except that safflower oil and detergent were not added. Instead, to a 1200 cc agar/gelatin $CuCl_2.2H_2O$ EDTA/NaCl/thimersal mixture at 55° C., 24 grams of 22 μm diameter glass beads were added. The mixture was cooled to 35° C. and 2.8 cc of formalin added. Finally, the resulting mixture is cooled to 30° C. and poured into the cylindrical opening in the phantom and allowed to congeal.

Figure 3:
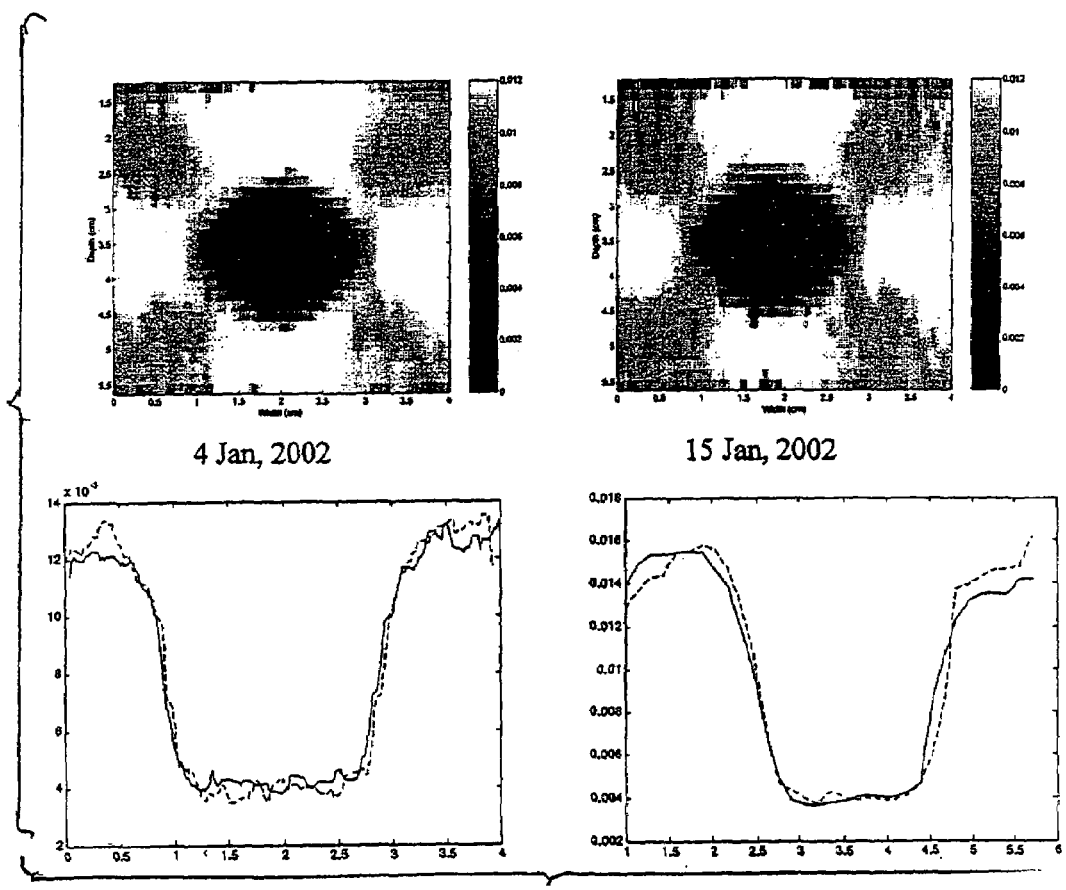
FIG. 3 shows ultrasound elastograms for a phantom composed of a 50% oil-in-agar/gelatin base material and an agar/gelatin inclusion, taken on two different days (Jan. 4, 2002, and Jan. 15, 2002). Also shown are the lateral (left) and axial (right) strain profiles taken on Jan. 4, 2002 (solid), and Jan. 15, 2002 (dashed). The vertical axis in the strain profiles represents strain and the horizontal axis represents centimeters.

FIG. 3 shows two ultrasound elastograms for the material of Example 3 taken eleven days apart. The ultrasound elastogram was acquired with a 7.5 MHz scan head with a 60% band width on a model SSD-2000 Aloka scanner.

Ultrasound, elastic, and magnetic resonance properties of the materials are listed in Tables 1 and 2.

Example 4

Cylindrical samples of tumor mimicking materials composed of gelatin suffused in a polymer mesh were made according to the following steps. These cylinders were in a shape providing for Instron measurement of Young's moduli. First, four polymer mesh cylinders having diameters of 2.5 cm and a heights of 1.0 cm were cut out of polymer mesh. Two of the cylinders were cut out of polyether mesh and two of the cylinders were cut out of polyurethane mesh. One of the polyurethane cylinders and one of the polyether cylinders had 10 cells per inch. The other two cylinders each had 30 cells per inch. Each of the cylinders was placed into a separate mold. A molten gelatin solution was made by combining 23.1 grams of dry weight calfskin gelatin in 150 ml of distilled water. The mixture was heated until it clarified at a temperature of about 90° C. at which time 0.15 grams of thimerosal per liter of mixture was added. The mixture was cooled to 35° C. and 7 ° ml of formalin solution per liter of the molten gelatin was added to the mixture. The molds were closed and baked at 50° C. for three days to allow the gelatin to congeal and crosslink. After three days the materials were removed from the molds and the excess gelatin was trimmed from the outside of the mesh.

Ultrasound, elastic, and magnetic resonance properties for the materials are listed in Tables 1 and 2.

Example 5

A heterogenous phantom was made where the inclusions and background are oil-in-gelatin emulsions, and where contrast results from differences in the oil concentrations in the materials. The gel matrix material has the same composition throughout the phantom as in the above examples.

A variable contrast "spherical lesion" phantom was made with 50% safflower oil-in-gelatin emulsion as the background material and three lower oil concentrations in the inclusions. Diagrams of two views of the phantom are shown in FIGS. 6 and 7. There were 3 sets of spheres made with 30% safflower oil, another 3 sets with 15% safflower oil and another 3 sets made with 0% safflower oil. Each set of spheres consist of a 3 mm, a 4 mm and a 6 mm-diameter sphere.

The gelatin matrix for all materials was made as follows. 750 cc of distilled water was combined with 115.4 grams of 200 bloom calfskin gelatin and brought to 90° C. until the mixture clarified. The molten gel was cooled to 55° C. and 0.75 grams of thimerosal was added to the mixture. The background materials was formed from 750 cc of the resulting molten gel by adding 750 cc of safflower oil at 55° C. and 16.7 cc of Ivory Liquid® detergent. Emulsification was produced by agitation with a spoon in a way that no air bubbles were introduced. Next, 4 grams per liter of 22 μm diameter glass beads were dispersed in the emulsion and it was cooled to 35° C. A 5.25 cc quantity of formalin was added and the molten gel cooled to 30° C. at which time the material was ready to be poured into a $10\times10\times10$ $cm^3$ mold for congealing.

Before the 50% oil-in-gelatin background material was introduced, all spherical inclusions were made and positioned in the $10\times10\times10$ $cm^3$ mold. The 30% oil-in-gelatin emulsion was made in the same fashion as the background except that the oil composed 30% by volume and the concentration of detergent was ⅗ of that in the background material. The concentration of formalin was kept proportional to the concentration of gelatin and the concentration of 22 μm diameter glass beads was kept at 4 grams per liter of the final emulsion. The 15% and 0% emulsions were produced accordingly.

For each oil concentration in the inclusion, spheres were made by immersing a two-part acrylic mold in the molten material and closing the mold. Each side of the mold has hemispherical depressions of the appropriate diameters. The depressions exist in flat surfaces and the depressions are positioned so that, when the two parts are brought together, the hemispheres align so that spherical volumes of molten gel are formed. Cylindrical pegs and holes assure proper alignment of the two parts of the mold. After the two parts of the mold have been brought together in the molten gel, the mold is removed and a C-clamp applied to keep the two parts together. Then the mold and C-clamp are attached to a rotation device and rotation at 2 rpm about a horizontal axis followed until the spheres have congealed. The first step in production of the phantom is to suspend the spheres on 0.3 mm-diameter stainless steel wires in the desired arrangement in the $10\times10\times10$ $cm^3$ mold. The molten background material (50% oil-in-gelatin) is introduced, the cavity sealed under positive gauge pressure, and the entire apparatus rotated at 2 rmp about a horizontal axis until congealing has completed. Twelve hours rotating is routine.

After congealing, the stainless steel wires are withdrawn leaving the solid spheres in the desired spatial arrangement and surrounded by the background material.

Ultrasound and elastic properties of the phantom component materials at 22° C. are given in Tables 1 and 2.

Note that neither the phantom nor test samples were baked at 50° C. following completion of the phantom. This explains the higher values of Young's moduli than for earlier similar materials, which had been baked.

It is noted that there is a difference in the way gel hardness is controlled in a heterogeneous phantom for the gelatin-only and the gelatin/agar tissue mimicking materials. Hardness differences in the gelatin materials relates to the concentration of oil in the emulsion. An oil emulsion is not necessary to make hardness differences in the gelatin/agar materials. With no oil in the gelatin/agar material, the gelatin concentration is kept constant everywhere, with the dry-weight agar concentration being the variable on which hardness depends. Oil emulsions can also be used with the gelatin/agar materials, if desired.

After the materials in Examples 1-5 were formed according to the methods above, the Young's moduli, the speed of sound in the materials, the attenuation coefficients, and, in some instances, the NMR relaxation times and elastic contrasts were measured at selected frequencies for each of the inclusion materials and each of the base materials. The results of these measurement are presented in Tables 1 and 2. In some cases, Table 2 includes Young's modulus values taken over the course of several months. Methods for taking ultrasound and NMR measurements are well known in the art and have been described previously in Madsen et al., "Interlaboratory comparison of ultrasonic backscatter, attenuation and speed," *J. Ultrasound in Med.* 18, 615-631 (1999); Blechinger et al., "Tissue mimicking gelatin-agar gels for use in magnetic resonance imaging phantoms," *Med. Phys.* 15, 629-636 (1988); and D'Souze et al., "Tissue mimicking materials for a multi-imaging modality prostate phantom," *Med. Phys.* 28, 688-700 (2001), which are incorporated herein by reference.

Briefly, the ultrasound parameters of the tissue mimicking materials were measured as follows for cyclindrical inclusions of the type described in the examples above. Tissue mimicking cylindrical inclusion samples were placed in a constant temperature water bath (maintained at 22° C.) between a transmitting transducer and receiving transducer. The parallel faces of the samples were maintained perpendicular to the ultrasound beam direction.

The speed of sound was measured by measuring the difference in the pulse arrival time for the cases in which the sample is present and absent between the transmitting and receiving transducer. The speed of sound in the tissue mimicking material sample was then calculated relative to the speed of sound in distilled water. The ultrasonic attenuation coefficient at four discrete frequencies was measured with the same experimental setup. This was done by noting the pulse amplitudes when the sample is present and absent from the path of the ultrasound beam. Corrections for the nonzero thickness of thin plastic layers over the parallel sample faces are significant for frequencies above about 2 MHz and are included in the data reduction.

For magnetic resonance imaging, hydrogen T1 and T2 relaxation times are parameters of interest. Measurements were performed on small samples in 5 mm diameter NMR tubes of the tissue mimicking materials of interest using a 40 MHz Minispec spectrometer (Bruker, Canada) along with supporting equipment consisting of an IBM computer, a storage oscilloscope, and a constant temperature water bath maintained at a temperature slightly below 22° C. The 40 MHz spectrometer probe is maintained at 40° C. In order to make measurements at 22° C., the sample placed in the water bath initially is then inserted in the spectrometer probe. Data is acquired within 1.5 minutes to avoid significant temperature rise of the sample. It has been shown that the temperature rise within the first minute is less than 2° C. The spectrometer was interfaced with the computer which uses software from IBM Instruments (Danbury, Conn.) for pulse programming and data acquisition. The optimum pulse durations were found by maximizing the initial signal for a 90° pulse and minimizing the absolute value of the entire free induction decay (FID) for the 180° pulse.

An inversion recovery (IR) sequence was used to obtain the data for the longitudinal relaxation time. A relaxation time (TR) of at least five times the expected T1 was used. The T1 experiment was repeated ten times. Data reduction was done by curve fitting to an expression of the form:

$$M(t)=M_0(1-2\exp(-t/T1))  \quad (1)$$

where M(t) is the instantaneous magnetization, $M_0$ is the initial longitudinal magnetization (thermal equilibrium), and t is the time at which each data point is acquired in the experiment. The uncertainty in the measurement of M(t) is calculated and this uncertainty is propagated to calculate the estimated uncertainty in T1.

The CPMG spin-echo pulse sequence was used to measure the transverse relaxation time. The relaxation delay (repetition time) was set to 5 times T1 and data was acquired for $\tau$ ($\tau$=one-half the echo time, TE) values of 25 µs, 125 µs, 250 µs, and 500 µs. 255 echo peaks were recorded in each CPMG sequence. The data obtained was fitted to a single exponential of the form:

$$M(t)=M_0\exp(-t/T2)  \quad (2)$$

where M(t) is the instantaneous magnetization at time t, $M_0$ is the initial magnetization and T2 is the transverse relaxation time.

The Young's modulus for each of the materials in Table 2 was obtained as follows. A hydraulic servo Instron™ 8500 from the University of Texas—Houston Dental School was employed. When measurements were not being made, the samples were stored in safflower oil to prevent dessication. First, a clean smooth flat plate was placed in the Instron machine and raised until it contacted a compressor. The compressor is connected directly to a load cell in the machine. When the load cell registered a load of 0.8 grams, the elevation of a reference point is recorded and used to zero the height of the samples. A cylindrical sample of the material to be characterized was removed from the safflower oil and placed on the flat plate in the Instron. A thin layer of oil clinging to each sample prevents desiccation of the material during the measurement and suppresses undesirable shear forces during the measurements. The system is then activated to cause the sample to come into contact with the compressor. Once a load of 0.8 grams was registered, the position was recorded and used to calculate the height of the sample. The Instron was programmed to apply a load yielding a 10% strain to the sample at a rate of 1% per second. After each test was recorded by the Instron, the system was returned to zero strain and the sample was given three minutes to recover. The procedure was repeated until the final load was less than one gram different than for the original measurement. If there was a load difference of more than one gram, the test was repeated four times and the data averaged for calculating the modulus over the strain range of 0-10%. The gel sample was then returned to the safflower oil for storage at room temperature. The test results were stored as stress-strain curves. The slope of the stress-strain curves yielded the value of E for each material.

TABLE 1

Values of Elastic, Ultrasound and Magnetic Resonance Properties of Tissue Mimicking Materials.

| Material | Ultrasound Propagation Speed (m/s) | Attenuation Coefficient/ Frequency (dB/cm/MHz) | T1(ms) | T2(ms) |
|---|---|---|---|---|
| Example 1: Gelatin Inclusion | 1536 | 0.179 | 1219 | 653 |
| Example 1: 50% Oil-in-Gelatin Base | 1496 | 0.320 | 452 | 285 |
| Example 2: Graphite-in-Gelatin Inclusion* | 1533 | 0.540 | | |
| Example 2: 32% Oil-in-Gelatin Base* | 1506 | 0.743 | | |
| Example 3: Agar/Gelatin Inclusion | 1516 | 0.188 | 787 | 127 |
| Example 3: 50% Oil-in-Agar/Gelatin Base | 1488 | 0.423 | 693 | 152 |
| Example 4: 10 Cells/inch Polyether (PE) in Gelatin Inclusion | | | | |
| Example 4: 30 Cells/inch Polyether in Gelatin Inclusion | | | | |
| Example 4: 10 Cells/inch Polyurethane in Gelatin Inclusion | | | | |
| Example 4: 30 Cells/inch Polyurethane in Gelatin Inclusion | | | | |
| Example 5: 50% Oil-in-Gelatin Base | 1497 | 0.38 | | |
| Example 5: 30% Oil-in-Gelatin Inclusion | 1514 | 0.32 | | |
| Example 5: 15% Oil-in-Gelatin Inclusion | 1526 | 0.28 | | |
| Example 5: 0% Oil-in-Gelatin Inclusion | 1540 | 0.15 | | |

TABLE 2

Values of Young's Modulus (E) over time and Elastic Contrast for Tissue Mimicking Materials.

| Material | Young's modulus (kPa) | | | | Elastic Contrast |
|---|---|---|---|---|---|
| | Day 1 | Day 105 | Day 120 | Day 158 | |
| Example 1: Gelatin Inclusion | | | | 27 | |
| Example 1: 50% Oil-in-Gelatin Base | | | | 10 | |
| Example 2: Graphite-in-Gelatin Inclusion* | 29, 29, 27 | | 38, 34, 36 | 41, 38, 37 | |
| Example 2: 32% Oil-in-Gelatin Base* | 16, 19, 17 | | 20, 20, 23 | 23, 25, 23 | |
| Example 3: Agar/Gelatin Inclusion | | | 13 | 13 | |
| Example 3: 50% Oil-in-Agar/Gelatin Base | | | 3 | 3 | |
| Example 4: 10 Cells/inch Polyether in Gelatin Inclusion | | 89 | 82 | 89 | |
| Example 4: 30 Cells/inch Polyester in Gelatin Inclusion | | 131 | 126 | 129 | |
| Example 4: 10 Cells/inch Polyurethane in Gelatin Inclusion | | 60 | 68 | 90 | |
| Example 4: 30 Cells/inch Polyurethane in Gelatin Inclusion | | 61 | 75 | 80 | |
| Example 5: 50% Oil-in-Gelatin Base | 40 | | | | 1.00 |
| Example 5: 30% Oil-in-Gelatin Inclusion | 66 | | | | 1.65 |
| Example 5: 15% Oil-in-Gelatin Inclusion | 86 | | | | 2.15 |
| Example 5: 0% Oil-in-Gelatin Inclusion | 103 | | | | 2.58 |

*3 test samples were made and measured

Example 6

This example demonstrates the effect of baking time on the Young's moduli of the gel-based materials of the invention. Four samples of plain gelatin, made according to the procedure in Example 1, and four samples of 50% oil-in-gelatin emulsion, also made according to the procedure in Example 1, were baked at 50° C. for baking times of between 0 and 15 days.

The Young's modulus for each material was measured according to the procedures outlined above at various intervals after baking was completed to illustrate the stability of the Young's moduli of the materials. The results of the measurements are shown in Tables 3 and 4.

TABLE 3

Young's Moduli for the Six Plain Gelatin Samples With Different 50° C. Baking Periods. The Samples Were Made on 28 Dec. 2002.

| Sample # | Number of Days Baked | Young's Modulus After... | | | | | |
|---|---|---|---|---|---|---|---|
| | | 19 Days | 31 Days | 55 Days | 88 Days | 111 Days | 142 Days |
| 1 | 0 | 104 | — | 123 | 115 | 106 | 107 |
| 2 | 5 | 31 | — | 33 | — | 34 | 31 |
| 3 | 10 | 22 | — | 29 | 27 | 27 | 25 |
| 4 | 15 | 17 | — | 28 | 24 | 22 | 24 |

TABLE 4

Young's Moduli for the Six 50% Oil-in-Gelatin Emulsoin Samples With Different 50° C. Baking Periods. The Samples Were Made on 28 Dec. 2002.

| Sample # | Number of Days | Young's Modulus After . . . | | | | | |
|---|---|---|---|---|---|---|---|
| | | 19 Days | 31 Days | 55 Days | 88 Days | 111 Days | 142 Days |
| 1 | 0 | 38 | — | 43 | 42 | 43 | 37 |
| 2 | 5 | 13 | — | 14 | — | 14 | 13 |
| 3 | 10 | 11 | — | 13 | 13 | 13 | 12 |
| 4 | 15 | 8 | — | 10 | 12 | 10 | 9 |

The data in Tables 3 and 4 show a pronounced decrease in the Young's moduli in the materials with increased baking time.

It is understood that the invention is not confined to the particular embodiments described herein, but embraces all such forms thereof as come within the scope of the following claims.

What is claimed is:

1. An human tumor tissue mimicking material for testing elastography imagers comprising an open-cell reticulated mesh material and a gel-forming material suffused into the mesh material, wherein the Young's modulus of the human tumor tissue mimicking material mimics the Young's modulus of human tumor tissue.

2. The human tumor tissue mimicking material of claim 1 wherein the Young's modulus of the human tumor tissue mimicking material is between about 10 and about 300 kPa.

3. The human tumor tissue mimicking material of claim 1 wherein the open-cell reticulated mesh material is a polyether mesh or a polyurethane mesh.

4. The human tumor tissue mimicking material of claim 1 wherein the open-cell reticulated mesh material comprises between about 10 and about 30 cells per inch.

5. The human tumor tissue mimicking material of claim 1 wherein the gel-forming material comprises gelatin.

6. The human tumor tissue mimicking material of claim 1 wherein the gel-forming material comprises agar.

7. The human tumor tissue mimicking material of claim 1 wherein the material is elastically nonlinear for strains of up to about 10 percent.

8. The human tumor tissue mimicking material of claim 1 wherein the gel-forming material further comprises at least one additional additive selected from the group consisting of a crosslinking agent, an organic hydroxy compound, microscopic solid particles, a copper salt, a chelating agent, and an agent for inhibiting attack by microorganisms.

9. The human tumor tissue mimicking material of claim 1 wherein the gel-forming material comprises an inner volume comprising agar suffused into the mesh material and an outer shell comprising gelatin suffused into the mesh material, wherein the outer shell surrounds the inner volume.

10. The human tumor tissue mimicking material of claim 9 wherein the outer shell comprises a mixture of agar and gelatin.

11. The human tumor tissue mimicking material of claim 10 wherein the inner volume is substantially spherically shaped and the outer shell has a plurality of spicules extending outward away from the inner volume.

12. A human tissue mimicking material for testing elastography imagers, comprising:

(a) a base material comprising a gel-forming material; and (b) at least one inclusion comprising the human tumor tissue mimicking material claim 1 at least partially surrounded by the base material, wherein the elastic contrast between the base material and the at least one inclusion is such that the elastic contrast between normal soft human tissue and human tumor tissue is mimicked, making the human tissue mimicking material suitable for use in testing elastography imagers.

13. The human tissue mimicking material of claim 12 wherein the elastic contrast between the base material and the at least one inclusion is between about 1 and about 4.

14. The human tissue mimicking material of claim 12 wherein the elastic contrast between the base material and the at least one inclusion is between about 1 and about 3.

15. The human tissue mimicking material of claim 12 wherein the speed of sound in the base material and the at least one inclusion is between about 1300 and 1650 m/s.

16. The human tissue mimicking material of claim 12 wherein the T1 values of the base material and the at least one inclusion are between about 200 ms and about 1200 ms and the T2 values of the base material and the at least one inclusion are between about 40 ms and about 200 ms, and further wherein T1 and T2 refer to hydrogen density and relaxation times.

17. The human tissue mimicking material of claim 12 wherein the elastic contrast between the base material and the at least one inclusion varies by less than about 20% over a period of at least six months.

18. The human tissue mimicking material of claim 12 wherein the gel-forming material in the base material is selected from the group consisting of gelatin, agar, or a mixture of gelatin and agar.

19. An elastography phantom comprising:

(a) an elastography phantom container enclosing an interior space; and (b) the human tissue mimicking material of claim 12 contained within the interior space of the container.

20. The human tumor tissue mimicking material of claim 1, wherein the open-cell reticulated mesh material is a polyurethane mesh.

21. The human tumor tissue mimicking material of claim 1, wherein the gel-forming material comprises an emulsion of oil-in-gelatin.

22. The human tumor tissue mimicking material of claim 1, wherein the gel- forming material comprises gelatin and agar.

23. The human tumor tissue mimicking material of claim 1, wherein the Young's modulus of the human tumor tissue mimicking material is 80 kPa.

24. The human tumor tissue mimicking material of claim 1, wherein the Young's modulus of the human tumor tissue mimicking material is 89 kPa.

25. The human tumor tissue mimicking material of claim 1, wherein the Young's modulus of the human tumor tissue mimicking material is from about 80 to about 300 kPa.

26. A method for testing an elastography imager comprising, mapping local elastic strains of a human tissue mimicking material to obtain a elastogram of the human tissue mimicking material, the human tissue mimicking material comprising:

(i) a base material comprising a gel-forming material; and
(ii) at least one inclusion of a defined shape at least partially surrounded by the base material, the at least one inclusion comprising an open-cell reticulated mesh material and a gel-forming material suffused into the mesh material, wherein the elastic contrast between the base material and the at least one inclusion is such that the elastic contrast between normal soft human tissue and human tumor tissue is mimicked.

27. The method of claim 26 wherein the elastogram is an ultrasound elastogram or a magnetic resonance elastogram.

* * * * *